(12) United States Patent
Sabottke et al.

(10) Patent No.: US 7,785,471 B2
(45) Date of Patent: Aug. 31, 2010

(54) CHROMATOGRAPHIC MEMBRANE SEPARATION

(75) Inventors: Craig Y. Sabottke, Annandale, NJ (US); Bal K. Kaul, Fairfax, VA (US); Dennis G. Peiffer, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 467 days.

(21) Appl. No.: 11/890,227

(22) Filed: Aug. 3, 2007

(65) Prior Publication Data

US 2008/0035566 A1 Feb. 14, 2008

Related U.S. Application Data

(60) Provisional application No. 60/836,327, filed on Aug. 8, 2006.

(51) Int. Cl.
| | |
|---|---|
| B01D 61/00 | (2006.01) |
| B01D 71/36 | (2006.01) |
| B01D 71/64 | (2006.01) |
| B01D 71/26 | (2006.01) |
| B01D 63/00 | (2006.01) |

(52) U.S. Cl. .............. 210/653; 210/652; 210/651; 210/500.39; 210/500.36

(58) Field of Classification Search .................. None
See application file for complete search history.

(56) References Cited

U.S. PATENT DOCUMENTS

| | | | |
|---|---|---|---|
| 4,650,574 A | 3/1987 | Hilgendorff et al. | |
| 4,853,128 A * | 8/1989 | Wrasidlo et al. | ............ 210/636 |
| 4,914,064 A | 4/1990 | Schucker | |
| 4,929,358 A | 5/1990 | Koenitzer | |
| 4,944,880 A | 7/1990 | Ho et al. | |
| 4,946,594 A | 8/1990 | Thaler et al. | |
| 4,962,270 A | 10/1990 | Feimer et al. | |
| 4,990,275 A | 2/1991 | Ho et al. | |
| 5,085,676 A * | 2/1992 | Ekiner et al. | ................ 96/13 |
| 5,130,017 A | 7/1992 | Schucker | |
| 5,138,023 A | 8/1992 | Sartori et al. | |
| 5,275,726 A | 1/1994 | Feimer et al. | |
| 5,445,731 A | 8/1995 | Tuohey et al. | |
| 5,550,199 A | 8/1996 | Ho et al. | |
| 5,670,051 A * | 9/1997 | Pinnau et al. | ................ 210/651 |
| 5,670,052 A | 9/1997 | Ho et al. | |
| 5,685,990 A | 11/1997 | Saugmann et al. | |
| 5,855,647 A | 1/1999 | Li et al. | |
| 6,096,114 A | 8/2000 | Li et al. | |
| 6,203,713 B1 | 3/2001 | Tanny | |
| 6,645,383 B1 | 11/2003 | Lee et al. | |
| 2004/0000513 A1 | 1/2004 | Colling et al. | |
| 2004/0004040 A1 | 1/2004 | Colling et al. | |
| 2006/0081500 A1 | 4/2006 | Bitterlich et al. | |

FOREIGN PATENT DOCUMENTS

| | | |
|---|---|---|
| WO | WO 2006/040307 A1 | 4/2006 |
| WO | WO 2006/066269 A2 | 6/2006 |

* cited by examiner

*Primary Examiner*—Krishnan S Menon

(57) ABSTRACT

This invention relates to a polymer membrane assembly for selective separation of permeate compositions by carbon weight. This invention also relates to a process for utilizing these polymer membrane assemblies in separation processes for selective carbon weight separation of hydrocarbon feedstreams components. More particularly, but not by way of limitation, this invention relates to the use membrane assemblies for the selective separation by carbon weight of aromatics from a hydrocarbon based feedstream.

24 Claims, 13 Drawing Sheets

Exploded Illustration of Membrane Assembly "D"

} PEI layer
  casting substrate

Illustration of Membrane Assembly "A"

———————————— 0.1 micron PTFE

} PEI layer
  0.1 micron PTFE

Exploded Illustration of Membrane Assembly "B"

Exploded Illustration of Membrane Assembly "C"

Exploded Illustration of Membrane Assembly "D"

Two-Stage Narrow Cut Separation Process Configuration

CHROMATOGRAPHIC MEMBRANE SEPARATION

CROSS-REFERENCE TO RELATED APPLICATIONS

This application is a United States utility application which claims priority to U.S. Provisional Patent Application Ser. No. 60/836,327, filed Aug. 8, 2006.

FIELD OF THE INVENTION

This invention relates to a polymer membrane assembly for selective separation of permeate compositions by carbon weight. This invention also relates to a process for utilizing these polymer membrane assemblies in separation processes for selective carbon weight separation of hydrocarbon feedstreams components. More particularly, but not by way of limitation, this invention relates to the use membrane assemblies for the selective separation by carbon weight of aromatics from a hydrocarbon based feedstream.

BACKGROUND OF THE INVENTION

Polymeric membrane based separation processes such as reverse osmosis, pervaporation and perstraction are conventional. In the pervaporation process, a desired feed component, e.g., an aromatic component, of a mixed liquid feed is preferentially absorbed by the membrane. The membrane is exposed at one side to a stream comprised of a mixture of liquid feeds and a vacuum is applied to the membrane at the opposite side so that the adsorbed component migrates through the membrane and is removed as a vapor from the opposite side of the membrane via a solution-diffusion mechanism. A concentration gradient driving force is therefore established to selectively pass the desired components through the membrane from its upstream side to its downstream side.

The perstraction process is utilized to separate a liquid stream into separate products. In this process, the driving mechanism for the separation of the stream into separate products is provided by a concentration gradient across the membrane. Certain components of the fluid will preferentially migrate across the membrane because of the physical and compositional properties of both the membrane and the process fluid, and will be collected on the other side of the membrane as a permeate. Other components of the process fluid will not preferentially migrate across the membrane and will be swept away from the membrane area as a retentate stream. Due to the pressure mechanism of the perstraction separation, it is not necessary that the permeate be extracted in the vapor phase. Therefore, no vacuum is required on the downstream (permeate) side of the membrane and the permeate emerges from the downstream side of the membrane in the liquid phase.

The economic basis for performing such separations is that the two products achieved through this separation process (i.e., retentate and permeate) have a refined value greater than the value of the unseparated the feedstream. Membrane technology based separations can provide a cost effective processing alternative for performing the product separation of such feedstreams. Conventional separation processes such as distillation and solvent extraction can be costly and energy intensive to install and operate in comparison with membrane process alternatives. These conventional based processes require substantial amounts of engineering, hardware and construction costs to install and then may require relatively high levels of operational and maintenance personnel and costs to maintain the facility in an operating status. Additionally, most of these processes require significant heating of the process streams in order to separate different components during the processing steps. This results in higher energy costs than are generally utilized by low-energy membrane separation processes.

In general, the membrane technology in the present art has the benefit of lower per unit energy costs per volume of separation than the conventional technologies in present art. However, a major obstacle in perfecting the commercial operation of membrane separation technologies is to improve the flux and selectivity of the current membrane systems in order to make the construction costs and capacity of membrane technologies economically viable on a refinery scale operation.

A myriad of polymeric membrane compositions have been developed over the years. Such compositions include polyurea/urethane membranes (U.S. Pat. No. 4,914,064); polyurethane imide membranes (U.S. Pat. No. 4,929,358); polyester imide copolymer membranes (U.S. Pat. No. 4,946,594); and diepoxyoctane crosslinked/esterified polyimide/polyadipate copolymer (diepoxyoctane PEI) membranes (U.S. Pat. No. 5,550,199).

The membranes and membrane assemblies of the prior art have been used in a configuration where a single cast layer of polymeric membrane material layer is cast either on glass, a layer of a polymer film casting substrate such as PTFE (polytetrafluoroethylene), or suitable fibrous materials that are used to facilitate the casting process and equipment. The type of casting substrate chosen affects the final membrane performance since the use of these membranes in a process application requires that the permeate be able to pass through the casting substrate as well as the cast polymeric membrane. The casting substrates of the prior art have been primarily utilized to provide a porous support which can provide the necessary mechanical strength upon which to the cast the polymeric membrane material during fabrication, in particular, when utilizing automated or semi-automated commercial fabrication equipment. It has therefore been a practice of the prior art to select the casting substrates mainly for maximizing mechanical strength while minimizing interference with the cast polymeric membrane's separation capabilities.

It is known by those of ordinary skill in the art that for a given cast polymeric membrane material, the change in the selectivity is generally independent of the thickness of the membrane and the flux is generally inversely proportional to the thickness of the membrane. Thus the direction of research in the art has been to find better membrane materials in order to achieve an improvement in the membrane selectivity and to improve the casting and mounting techniques of polymer membranes to allow thinner operational castings in order to achieve an improvement in membrane flux.

The current art has modified these single casting layer membranes by varying membrane parameters such as the membrane composition, fabrication and curing processes, and process uses. However, a characteristic of these supported and unsupported single layer polymeric membranes that are utilized for hydrocarbon service aromatic/non-aromatic separations is that the aromatics in the permeate have a similar carbon weight distribution as the aromatics in the feed. That is to say, that the concentration of a specific carbon weight aromatic in the permeate is substantially proportional to the concentration of the same carbon weight aromatic in the feed. This is true across the carbon weight spectrum of the feed and permeate aromatics.

However, in some applications, certain carbon weight aromatic or carbon weight ranges of aromatics may be more beneficial as a product than mixed with other aromatics that are present in the feedstream. An example of this is in gasoline production where higher weight aromatics, for example $C_7$ and above in the gasoline range material, generally have a higher octane value than the lower weight aromatics, such as $C_6$ and below. Therefore, it would be beneficial in a membrane separation process if a shift in the average carbon weight of the aromatics in the permeate could be made with respect to the average carbon weight of the aromatics in the feed. Not only would such a process result in a higher value final product, but alternate methods of obtaining a similar product using conventional techniques would generally require higher installation and operating costs than if this segregation by carbon weight could be accomplished simultaneous with the aromatics/non-aromatics separation in the membrane separation process. The processes known in the art to make this secondary separation, such as a distillation step prior to or after the aromatic separation of the process by the membrane assembly, generally require more capital and energy costs than if a single-step, low-energy membrane separation process could provide a similar separation by selectively separating aromatics by carbon weight.

SUMMARY OF THE INVENTION

The present invention includes improved membrane compositions and membrane assembly configurations for the selective separation by carbon weight of aromatics from a hydrocarbon based feedstream.

In a preferred embodiment, the present invention is a membrane assembly for separating aromatics from a hydrocarbon feedstream containing aromatics and non-aromatics, wherein said membrane assembly is comprised of at least two polymeric membrane elements and at least two polymer films, wherein a retentate stream and a permeate stream are extracted from the membrane assembly, and wherein at least one polymeric membrane element is comprised of a dianhydride, a diamine, a cross-linking agent and a difunctional dihydroxy polymer selected from:

a) dihydroxy end-functionalized ethylene propylene copolymers with an ethylene content from about 25 wt % to about 80 wt %;

b) dihydroxy end-functionalized ethylene propylene diene terpolymers with an ethylene content from about 25 wt % to about 80 wt %;

c) dihydroxy end-functionalized polyisoprenes; dihydroxy end-functionalized polybutadienes; dihydroxy end-functionalized polyisobutylenes;

d) dihydroxy end-functionalized acrylate homopolymers, copolymers and terpolymers; dihydroxy end-functionalized methacrylate homopolymers, copolymers and terpolymers; and mixtures thereof,
wherein the mixtures of acrylate and methacrylate monomers range from $C_1$ to $C_{18}$;

e) dihydroxy end-functionalized condensation homopolymers, copolymers, terpolymers and higher order compositions of structurally different monomers, including alcohol-terminated end-functionalized esters and dihydroxy end-functionalized multimonomer polyesters; and mixtures thereof;
wherein the polyalkyladipate structures range from $C_1$ to $C_{18}$;

f) dihydroxy end-functionalized perfluoroelastomers;

g) dihydroxy end-functionalized urethane homopolymers, copolymers, terpolymers, and higher order compositions of structurally different monomers;

h) dihydroxy end-functionalized carbonate homopolymers, copolymers, terpolymers, and higher order compositions of structurally different monomers;

i) dihydroxy end-functionalized ethylene alpha-olefin copolymers; dihydroxy end-functionalized propylene alpha-olefin copolymers; and dihydroxy end-functionalized ethylene propylene alpha-olefin terpolymers;
wherein the alpha-olefins are linear or branched and range from $C_3$ to $C_{18}$;

j) dihydroxy end-functionalized styrene homopolymers, copolymers, terpolymers, and higher order compositions of structurally different monomers;

k) dihydroxy end-functionalized silicone homopolymers, copolymers, terpolymers, and higher order compositions of structurally different monomers;

l) dihydroxy end-functionalized styrene butadiene copolymers; dihydroxy end-functionalized styrene isoprene copolymers; and m) dihydroxy end-functionalized styrene butadiene block copolymers; and dihydroxy end-functionalized styrene isoprene block copolymers.

In a more preferred embodiment, at least one polymeric membrane element of the membrane assembly is comprised of a hard segment and a soft segment, and the soft segment has a glass transition temperature, $T_g$, of less than 77° F. (25° C.).

In another preferred embodiment, the Absorbance Infrared Spectrum of at least one polymeric membrane element of the membrane assembly has an Aliphatic C-H Area to Aromatic C-H Area ratio of at least 10.

In an even more preferred embodiment, the membrane assembly, when subjected to a hydrocarbon feed comprised of $C_7$ to $C_{12}$ aromatics and non-aromatics under pervaporation conditions, is capable of a selective separation of aromatic by carbon weight wherein at least one $C_{n+1}$ permeate aromatic wt %:$C_{n+1}$ feed aromatic wt % ratio is at least 100% greater than the $C_n$ permeate aromatic wt %:$C_n$ feed aromatic wt % ratio.

In another embodiment, the membrane assembly of the present invention may be utilized in a process for separating aromatics from a hydrocarbon feedstream containing aromatics and non-aromatics comprising:

a) contacting one side of a membrane assembly with a hydrocarbon steam, wherein the membrane assembly is comprised at least two polymeric membrane elements and at least two polymer films, and b) extracting a permeate stream from the opposite side of the membrane assembly;

wherein the weighted average of the carbon weights of the aromatics in the permeate stream is at least one carbon weight higher than the weighted average of the carbon weights of the aromatics in the feedstream.

In yet another embodiment, two membrane assemblies of the present invention may be utilized in a process for separating aromatics from a hydrocarbon feedstream containing aromatics and non-aromatics comprising:

a) contacting a first polymeric membrane assembly with a first carbon weight aromatic cut-point, resulting in a first retentate and a first permeate;

b) contacting the first permeate is contacted with a second polymeric membrane assembly with a second carbon weight aromatic cut-point, wherein the second carbon weight aromatic cut-point that is higher than the first carbon weight aromatic cut-point of the first polymeric membrane assembly, resulting in a second retentate and a second permeate;

wherein no more than two consecutive carbon weight aromatics comprise at least 75 wt % of the total aromatics in the second retentate, and wherein the combined wt % of the two consecutive carbon weight aromatics in said second retentate is at least 100% greater than the combined wt % of the two consecutive carbon weight aromatics in the hydrocarbon feedstream.

In this fashion, a product stream that possesses a high concentration of a narrow range carbon weight aromatic hydrocarbon may be obtained.

DETAILED DESCRIPTION OF THE PREFERRED EMBODIMENTS

Figure 1:
FIG. 1 is an illustration of the membrane assembly configuration of a single layer of a polyimide/aliphatic polyester membrane cast upon a PTFE polymer film. This membrane assembly is designated as "Assembly A", and replicates a comparable single layer cast membrane configuration.

The present invention solves the present problem of the art by utilizing multiple polymer membrane elements and polymer membrane films in a membrane assembly to selectivity separate a hydrocarbon feedstream by a combination of polarity and carbon weight into permeate products. It has been discovered that when the membrane assemblies of the present invention, which are comprised of a multiple polymeric membrane elements, are subjected to a hydrocarbon feed containing aromatics and non-aromatics, that the resultant aromatic rich permeate is unexpectedly shifted toward higher concentrations of higher carbon weight aromatics. This invention retains the benefits of polarity separation with an added advantage of shifting the boiling point. In addition, it has also been discovered that certain polymeric film materials utilized in series with select polymer membrane materials can achieve an unexpected shift in the average carbon weight of the permeate product and may also be used to make a lower carbon weight cut-off of the permeate through the proper selection of a polymeric film with characteristics that will reject certain vapor point materials under selected conditions.

It would be beneficial at this point to provide definitions for some of the terms used herein as follows. The term "hydrocarbon" as used herein means an organic compound having a predominantly hydrocarbon character. Accordingly, organic compounds containing one or more non-hydrocarbon radicals (e.g., sulfur or oxygen) would be within the scope of this definition. As used herein, the terms "aromatic hydrocarbon" or "aromatic" means a hydrocarbon-based organic compound containing at least one aromatic ring. The rings may be fused, bridged, or a combination of fused and bridged. In a preferred embodiment, the aromatic species separated from the hydrocarbon feed contains one or two aromatic rings. The terms "non-aromatic hydrocarbon" or "non-aromatic" or "saturate" means a hydrocarbon-based organic compound having no aromatic cores. Also as used herein, the term "selectivity" means the ratio of the desired component(s) in the permeate to the non-desired component(s) in the permeate divided by the ratio of the desired component(s) in the feedstream to the non-desired component(s) in the feedstream. Also, the term "flux" or "normalized flux" is defined as the mass rate of flow of the permeate across a membrane, normally expressed in units of Kg/m$^2$-day, Kg/m$^2$-hr, Kg-μm/m$^2$-day, or Kg-μm/m$^2$-hr. The terms "carbon molecular weight" or "carbon weight" used herein refers to the number of carbon atoms in a hydrocarbon molecule. As such, a hydrocarbon molecule with three carbon atoms (e.g., a $C_3$ molecule, such as propane) would have a carbon molecular weight or carbon weight of 3, and a hydrocarbon molecule with four carbon atoms (e.g., a $C_4$ molecule, such as butane) would have a carbon molecular weight or carbon weight of 4. The term "molecular weight cut-point" as used herein is used to define hydrocarbon molecules that have a carbon molecular weight equal to or lower than the cut-point specified. The terms "average carbon weight" or "the weighted average of the carbon weights" as used herein are to denote the average carbon weight of the hydrocarbon in the designated stream, feed, or product. This calculated by the multiplying each carbon weight hydrocarbon in the stream by its corresponding weight % of the hydrocarbons in the stream, summing these values and dividing by 100. It should be noted that all non-hydrocarbon components are to be deducted out of the total weight of the stream being measured before the calculation is made. Thus this calculation is based solely on the hydrocarbon components in the stream defining a 100 wt %. For example, in a stream where the hydrocarbon portion of the stream is comprised of 10 Wt % $C_7$s, 50 wt % $C_8$s, and 40 wt % $C_9$s, the average carbon weight is:

$$\frac{[(10)*(7)] + [(50)*(8)] + [(40)*(9)]}{100} = 8.3 \text{ Average Carbon Weight}$$

It has been discovered that through proper selection of membrane sheet materials and compositions, in conjunction with the proper membrane assembly configuration and operating properties, that the weighted average of the carbon weight of the permeate aromatic content can be shifted with respect to the weighted average of the carbon weight of the feed aromatic content. In a preferred embodiment of the present invention, it has been discovered that with the proper selection of polymer membrane elements, polymer films and the operating pressures and temperatures of the membrane separation process, that a substantially accurate lower carbon weight cut-point may be made with respect to the permeate obtained. In other words, with properly selected materials, configuration and operating conditions, the membrane assembly can be made to substantially reject all aromatics at and below a designated carbon weight (e.g., $C_7$s and below, or $C_8$s and below, etc.) with little effect to the quantity of aromatics that are transmitted through the membrane that are of the next higher carbon weight. For example, a membrane assembly of the present invention can be designed to reject substantially all $C_{7-}$ aromatics from transmitting through the membrane to the permeate while having little detrimental effect on the $C_{8+}$ aromatics transmission through the membrane assembly to the permeate product.

FIG. 1 shows a membrane assembly configuration comprised of one polymer membrane element and one polymer film. In this configuration, a polyimide/aliphatic polyester membrane material was cast upon a PTFE substrate to simulate a single polymer membrane/single polymer film configuration for comparison with the multi-membrane/film assemblies of the present invention. This test membrane assembly is designated "Assembly A" in a configuration as shown in FIG. 1. Details of the membrane assembly and the process testing conditions are given in Example 1.

Membrane Assembly A was configured to show the separation properties of a single polymer membrane/single polymer film configuration with respect to carbon weight separation to hydrocarbons feeds comprised of aromatics and non-aromatics. Assembly A was tested in a heavy cat naphtha feed service. The results of the testing of this membrane assembly are graphically shown in FIG. 5. As can be seen, the results are typical of a single polymeric membrane configuration where the wt % of the aromatics in the permeate of each carbon weight follow a similar distribution to the wt % of the same carbon weight aromatics in the feed. In this configuration, there is almost no distinction between the permeate aromatics distribution and the feed aromatics distribution by carbon weight.

Figure 2:
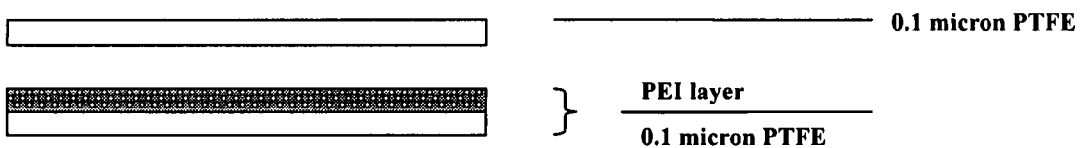
FIG. 2 is an exploded illustration of one membrane assembly configuration of the present invention comprised of a cast layer of a polyimide/aliphatic polyester membrane on a PTFE film in conjunction with a separate layer of PTFE film added to the face of the polyimide/aliphatic polyester membrane. This membrane assembly is designated as membrane "Assembly B".

Membrane "Assembly B" is shown in FIG. 2 and illustrates one embodiment of a membrane assembly of the present invention. Here, a thin PTFE membrane film was added to the top, or feed side, face of polymeric membrane/film assembly configuration similar to Assembly A. Assembly B was then tested in heavy cat naphtha feed service and details of the membrane assembly and the process testing conditions are shown in Example 2. The results of the process testing of this membrane assembly are graphically shown in FIG. 6. Here, one of the aspects of the present invention can be seen, where the membrane assembly rejected almost all of the $C_7$ and lighter aromatics from passing through the membrane assembly into the permeate. By utilizing this configuration of the membrane assembly, a nearly clean cut-point can be made in the permeate at a certain carbon weight aromatic and below, in this case $C_7$ aromatics and below, while allowing the heavier aromatics, in this case $C_8$ aromatics and above, to pass through the membrane virtually unaffected.

Figure 3:
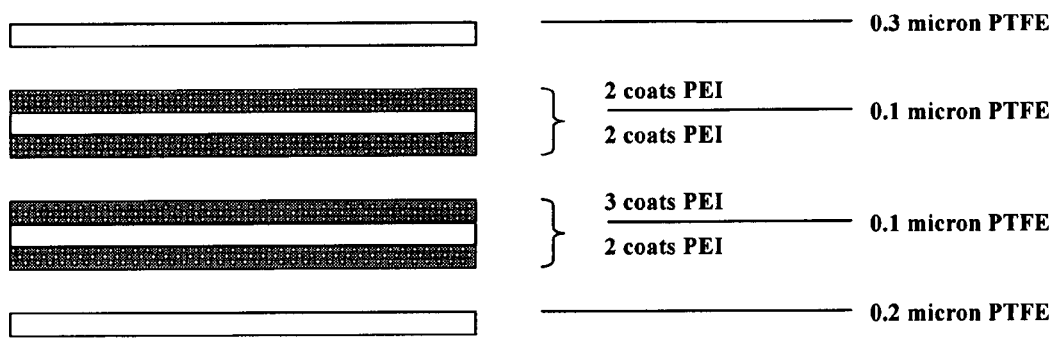
FIG. 3 is an exploded illustration of another possible membrane assembly configuration of the present invention comprised of multiply stacked cast layers of polyimide/aliphatic polyester membranes on PTFE films and separate layers of PTFE. This membrane assembly is designated as membrane "Assembly C".

FIG. 3 illustrates another embodiment of a multilayered polymeric membrane assembly of the present invention. This membrane assembly is designated as "Assembly C" and was tested for its separation properties in a gasoline feed service. This membrane assembly was fabricated from multiple polyimide/aliphatic polyester membranes elements and sheets of a polymer (in this case, PTFE) film. Details of the membrane assembly and the process testing conditions can be seen in Example 3. The process test results for Assembly C are graphically illustrated in FIG. 7.

Figure 7:
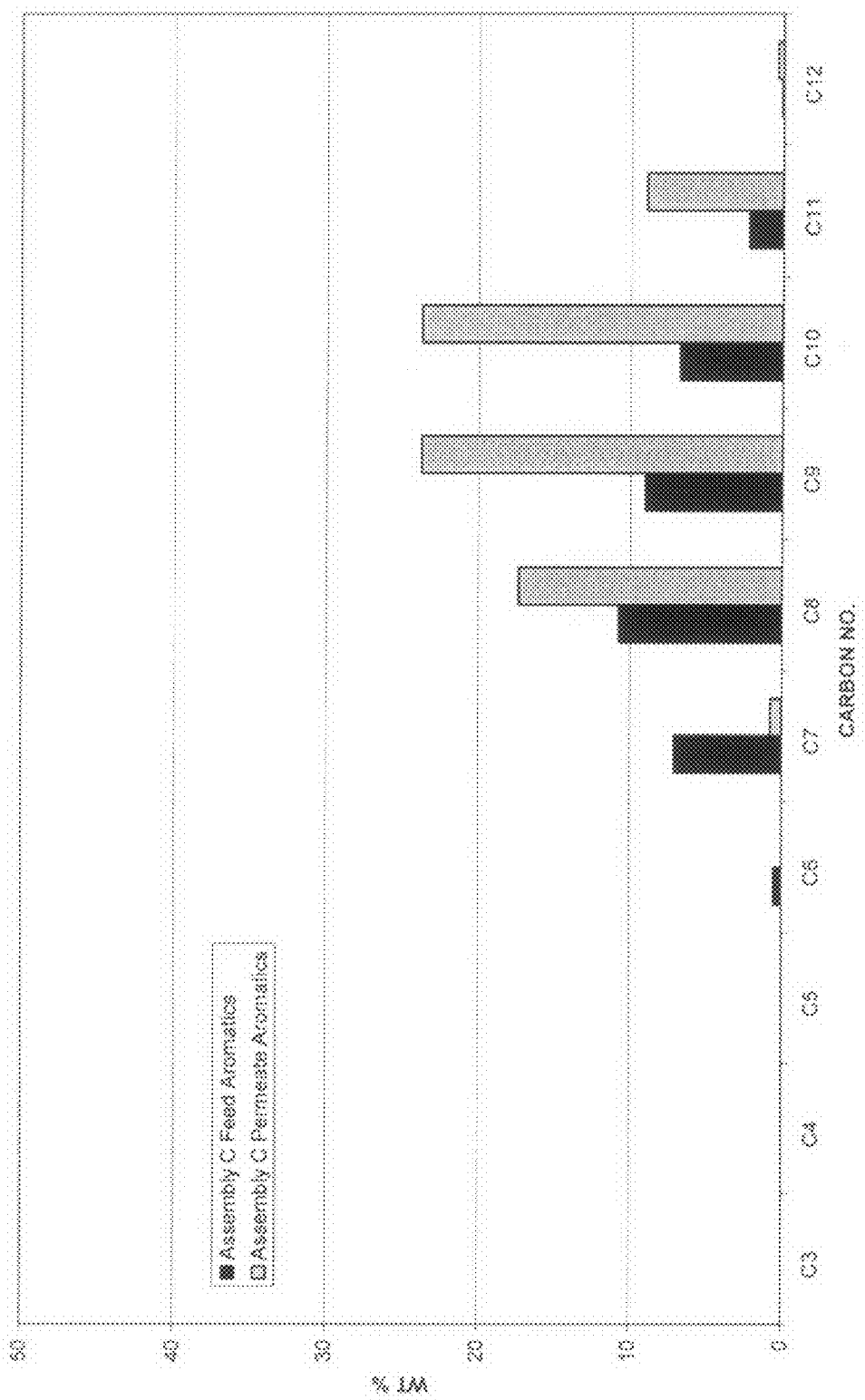
FIG. 7 is graph showing the process separation results of a multiply stacked cast layers of a PEI membrane on PTFE and separate layers of PTFE (membrane "Assembly C") subject to a gasoline feed.

It can be seen in FIG. 7 that even with the higher concentration of the lighter hydrocarbon components of this gasoline feed as compared to the heavy cat naphtha feed used in Examples 1 and 2, this multiple polymer membrane element/multiple polymer film assembly was able to eliminate almost all of the $C_7$ and lighter aromatics from passing through the membrane assembly to the permeate. Here the permeate aromatic content was significantly shifted to the heavier aromatics, in particular the $C_8$ and above aromatics, with maximum permeate concentrations around the $C_9$ to $C_{10}$ aromatics.

Figure 4:
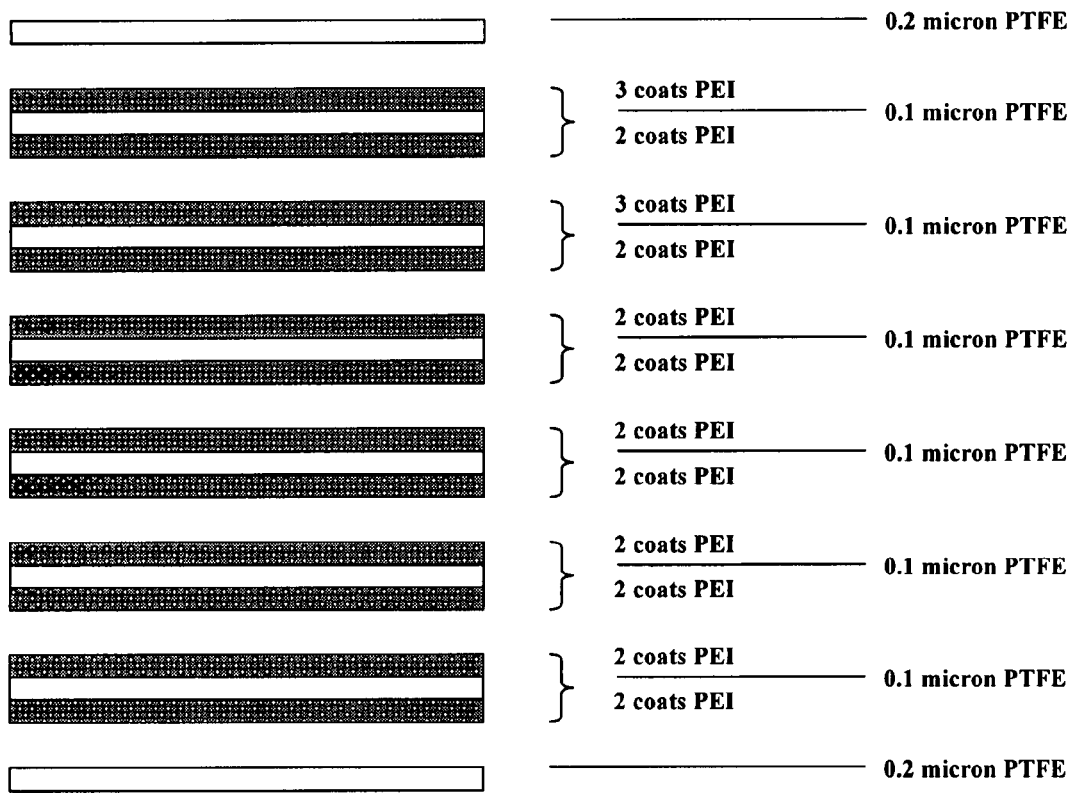
FIG. 4 is an exploded illustration of still another possible membrane configuration of the present invention comprised of multiply stacked cast layers of polyimide/aliphatic polyester membranes on PTFE films and separate layers of PTFE. This membrane assembly is designated as membrane "Assembly D".
Figure 8:
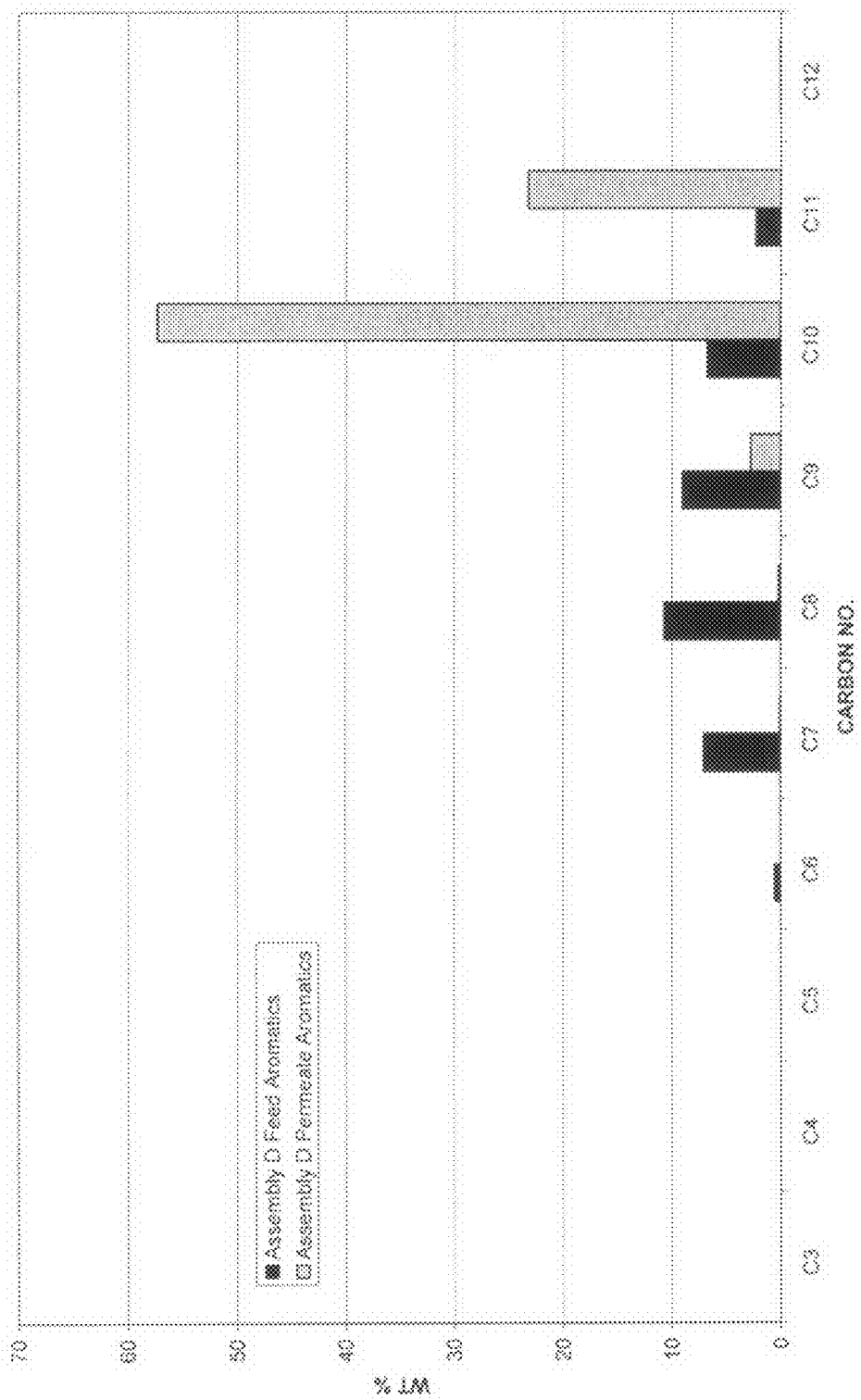
FIG. 8 is graph showing the process separation results of a multiply stacked cast layers of a PEI membrane on PTFE and separate layers of PTFE (membrane "Assembly D") subject to a gasoline feed.

In order to further test this unexpected discovery of the ability to shift the carbon weight content of the permeate through selective stacking of membrane elements, a membrane assembly with a greater number of polymer membrane elements and polymer films than Assembly C was fabricated and tested in a similar gasoline feed service. This membrane assembly is shown in FIG. 4 and designated as "Assembly D". It is yet another embodiment of the membrane assemblies of the current invention. Details of the membrane assembly and the process testing conditions are shown in Example 4. The process test results for Assembly D are graphically illustrated in FIG. 8. As can be seen from FIG. 8, membrane Assembly D, similar to Assembly C, resulted in a shift with respect to the feed of the permeate to the heavier aromatics. As shown in FIG. 7, the permeate product from Assembly C was shifted to primarily the $C_9$ to $C_{10}$ weight aromatics, while as shown in FIG. 8, the permeate product from Assembly D, which was comprised of additional membrane elements, was shifted to primarily the $C_{10}$ to $C_{11}$ weight aromatics. These results show the unexpected results that an incremental increase in the number of membrane elements and polymer film layers can yield an incremental increase in the average carbon weight of the aromatic composition of the permeate.

In addition to the discovery of the permeate carbon weight shifting, by comparing the results of FIG. 7 and FIG. 8, it can be seen that the carbon weight cut-point, or carbon weight below which substantially none of the carbon weight material at or below this carbon weight are allowed to pass through the membrane, has been surprisingly shifted to even higher carbon weights. In comparing FIG. 7 and FIG. 8, it can be seen that the carbon weight cut-point has been shifted from approximately $C_7$ material, as was the case of Assembly C which results are shown in FIG. 7, to approximately $C_8$ material, as is the case of Assembly D which results are shown in FIG. 8.

In summary, the membrane assemblies of the present invention can be tailored to achieve the unexpected result of changing the carbon weight composition of the aromatics in the permeate. While not wishing to be held to any specific theory, it is believed that an increase in polymeric membranes elements affects the transport properties of the aromatic material flow across the membranes. It is believed that the increased number of membrane interfaces and the associated concentration gradients at the interfaces of the separate membrane layers selectively restrict the diffusion of the lower carbon weight aromatics through the membrane. As the number of these interfaces increases, it is believed that the transport potentials of the higher carbon weight aromatics preferentially increase with respect to the lower carbon weight aromatics. This results in a incrementally higher carbon weight aromatic at each of the proceeding interfaces which results in a final higher carbon weight product that is recovered on the permeate side of the membrane.

The present invention provides the useful and unexpected capability of segregating higher carbon weight aromatics from lower carbon weight aromatics in a single membrane separation process. In accordance with this invention, at least one polymeric membrane element in the membrane assembly of the present invention is comprised of a dianhydride, a diamine, a cross-linking agent and a difunctional dihydroxy polymer selected from:

a) dihydroxy end-functionalized ethylene propylene copolymers with an ethylene content from about 25 wt % to about 80 wt %;
  b) dihydroxy end-functionalized ethylene propylene diene terpolymers with an ethylene content from about 25 wt % to about 80 wt %;
  c) dihydroxy end-functionalized polyisoprenes; dihydroxy end-functionalized polybutadienes; dihydroxy end-functionalized polyisobutylenes;
  d) dihydroxy end-functionalized acrylate homopolymers, copolymers and terpolymers; dihydroxy end-functionalized methacrylate homopolymers, copolymers and terpolymers; and mixtures thereof,
  wherein the mixtures of acrylate and methacrylate monomers range from $C_1$ to $C_{18}$;
  e) dihydroxy end-functionalized condensation homopolymers, copolymers, terpolymers and higher order compositions of structurally different monomers, including alcohol-terminated end-functionalized esters and dihydroxy end-functionalized multimonomer polyesters; and mixtures thereof;
  wherein the polyalkyladipate structures range from $C_1$ to $C_{18}$;
  f) dihydroxy end-functionalized perfluoroelastomers;
  g) dihydroxy end-functionalized urethane homopolymers, copolymers, terpolymers, and higher order compositions of structurally different monomers;
  h) dihydroxy end-functionalized carbonate homopolymers, copolymers, terpolymers, and higher order compositions of structurally different monomers;
  i) dihydroxy end-functionalized ethylene alpha-olefin copolymers; dihydroxy end-functionalized propylene alpha-olefin copolymers; and dihydroxy end-functionalized ethylene propylene alpha-olefin terpolymers;
  wherein the alpha-olefins are linear or branched and range from $C_3$ to $C_{18}$;
  j) dihydroxy end-functionalized styrene homopolymers, copolymers, terpolymers, and higher order compositions of structurally different monomers;
  k) dihydroxy end-functionalized silicone homopolymers, copolymers, terpolymers, and higher order compositions of structurally different monomers;
  l) dihydroxy end-functionalized styrene butadiene copolymers; dihydroxy end-functionalized styrene isoprene copolymers; and
  m) dihydroxy end-functionalized styrene butadiene block copolymers; and dihydroxy end-functionalized styrene isoprene block copolymers.

In a preferred embodiment, at least one membrane element in the membrane assembly of the present invention is comprised of a dianhydride, a diamine, a cross-linking agent and a difunctional dihydroxy polymer selected from:

a) dihydroxy end-functionalized condensation homopolymers, copolymers, terpolymers and higher order compositions of structurally different monomers, including alcohol-terminated end-functionalized esters and dihydroxy end-functionalized multimonomer polyesters; and mixtures thereof;
  wherein the polyalkyladipate structures range from $C_1$ to $C_{18}$;
  b) dihydroxy end-functionalized perfluoroelastomers;
  c) dihydroxy end-functionalized urethane homopolymers, copolymers, terpolymers, and higher order compositions of structurally different monomers;
  d) dihydroxy end-functionalized carbonate homopolymers, copolymers, terpolymers, and higher order compositions of structurally different monomers;
  e) dihydroxy end-functionalized ethylene alpha-olefin copolymers; dihydroxy end-functionalized propylene alpha-olefin copolymers; and dihydroxy end-functionalized ethylene propylene alpha-olefin terpolymers;
  wherein the alpha-olefins are linear or branched and range from $C_3$ to $C_{18}$; and
  f) dihydroxy end-functionalized silicone homopolymers, copolymers, terpolymers, and higher order compositions of structurally different monomers.

In a even more preferred embodiment of the present invention, at least one membrane element in the membrane assembly is comprised of a dianhydride, a diamine, a cross-linking agent and a difunctional dihydroxy polymer selected from:

a) dihydroxy end-functionalized condensation homopolymers, copolymers, terpolymers and higher order compositions of structurally different monomers, including alcohol-terminated end-functionalized esters and dihydroxy end-functionalized multimonomer polyesters; and mixtures thereof;
  wherein the polyalkyladipate structures range from $C_1$ to $C_{18}$;
  b) dihydroxy end-functionalized perfluoroelastomers;
  c) dihydroxy end-functionalized carbonate homopolymers, copolymers, terpolymers, and higher order compositions of structurally different monomers; and
  d) dihydroxy end-functionalized ethylene alpha-olefin copolymers; dihydroxy end-functionalized propylene alpha-olefin copolymers; and dihydroxy end-functionalized ethylene propylene alpha-olefin terpolymers;
wherein the alpha-olefins are linear or branched and range from $C_3$ to $C_{18}$.

Preferred embodiments and additional details of the polymer compositions and their fabrication are more fully described in a concurrently filed, co-pending U.S. Provisional Patent Application Ser. No. 60/836,423 filed on Aug. 8, 2006 and its corresponding U.S. Utility patent application Ser. No. 11/890,225 entitled "Chemically Cross-Linked Polymeric Membranes and Method of Use" which is herein incorporated by reference and as shown in Examples 5 and 6 herein. Polymer membrane elements of the present invention may utilize membranes compositions as disclosed herein and as disclosed in Patent Application Ser. No. 60/836,423 and its corresponding U.S. Utility patent application.

It should be made clear that the terms "polymeric membrane elements" or "membrane elements" as used herein means a copolymer membrane not including the casting support for the membrane element. A single membrane element may be comprised of a single layer (or "coat") of a polymer. However, a single membrane element, as defined herein, may also be comprised of one or more integral polymer layers (or "coats") wherein the multiple layers of polymer solutions are integrated in layers and then chemically crosslinked to form an integrally-layered membrane element which possesses a continuous, fused membrane structure wherein the individual layers retain their separate structural and diffusivity properties. Preferred embodiments and additional details of the integrally-layered membrane elements as utilized herein are more fully described in a concurrently filed, co-pending U.S. Patent Application Ser. No. 60/836,424 filed on Aug. 8, 2006 and its corresponding U.S. Utility patent application Ser. No. 11/890,224 entitled "Integrally-Layered Polymeric Membranes and Method of Use" which is herein incorporated by reference, and as embodiments are disclosed herein and further illustrated in Example 7 herein.

As defined herein, the layers or coats for an element must not be separated by a polymeric film or casting support; if so, then they are counted as two separate membrane elements. The term "polymer film" as used herein applies to polymer film materials whether they are incorporated directly onto a membrane element, incorporated as separate sheets in the membrane assembly, or whether they are utilized as a casting substrate for a membrane element. All polymer film sheets in a membrane assembly of the present invention, regardless of how they are used, are counted as a film or sheet as used herein. In a preferred embodiment, the membrane assembly of the present invention is comprised of at least one integrally-layered membrane element, more preferably at least two integrally-layered membrane elements, and even more preferably at least three integrally-layered membrane elements.

Also, as part of the present invention, it has unexpectedly been discovered that carbon weight "cut-points" can be made in the aromatic permeate resulting from the membrane assemblies of the present invention. While not wishing to be held to any particular theory, it is believed that the pore size of the polymer film layers, such as the PTFE layers utilized in the membrane examples herein, plays a synergistic role with the membrane layering to obtain the carbon weight cut-point selectivities of the present invention. The selection of the type and quantity of these polymer films in conjunction with the operating temperature and pressures of the system can be selected and oriented in a manner to preferentially allow larger carbon weight aromatic molecules to pass through the polymer films while preferentially excluding the lower carbon weight molecules. It is believed that similar to the carbon weight concentration shift of the present invention as described above, the cut point selection at the interfaces also affects the final cut-point due to the distinct pressure gradients across the staged membrane assembly and the possible vaporization of lighter carbon weight materials at these interfaces. Carbon weight concentrations collecting at these interfaces may also have an affect on the transport properties of the polymer films.

The membrane assemblies of the present invention must include at least one polymeric membrane element and at least two polymer films. In a preferred embodiment, the membrane assembly of the present invention is comprised of at least two polymeric membrane elements and at least two polymer films. More preferably, the membrane assembly is comprised of at least three polymeric membrane elements and at least three polymer films.

While there is theoretically no upper limit to the number of polymeric membrane elements, membrane element layers, or polymer films, in another preferred embodiment, the membrane assembly of the present invention is comprised of about 1 to about 30 polymeric membrane elements and from about 2 to about 20 polymeric film layers. More preferable, the membrane assembly of the present invention is comprised of about 2 to about 25 polymeric membrane elements and from about 2 to about 15 polymeric film layers.

In a preferred embodiment, embodiment, the present invention includes the composition and use of at least one polymer membrane element comprising soft and hard polymer segments wherein the glass transition temperature, ($T_g$), of the soft segment is less than 25° C. The term glass transition temperature, ($T_g$), is well known in the art and is defined in *Thermal Characterization of Polymeric Materials* (E. A. Turi ed., Academic Press, NY, 1981). It should be noted that the glass transition temperature measurements as defined herein are measured on a final composition, cured, and "unswollen" polymer membrane (i.e., no post-cure solvents).

In a preferred embodiment, at least one polymer membrane element of the membrane assembly of the present invention is comprised of a hard segment and soft segment, and the glass transition temperature, $T_g$, of the soft segment is less than 77° F. (25° C.), more preferably less than 32° F. (0° C.), and even more preferably less than −13° F. (−25° C.), most preferably less than −58° F. (−50° C.). In another embodiment, at least one polymer membrane element of the membrane assembly also has a hard segment $T_g$ of greater than 212° F. (100° C.), preferably greater than 248° F. (120° C.).

In a more preferred embodiment of the present invention, at least one polymer membrane element is an integrally-layered membrane element comprised of a hard segment and soft segment with at least one membrane layer having a glass transition temperature, $T_g$, of the soft segment of less than 77° F. (25° C.), preferably less than 32° F. (0° C.), more preferably less than −13° F. (−25° C.) and most preferably less than −58° F. (−50° C.). In yet another more preferred embodiment, at least one polymer membrane element is an integrally-layered membrane element with at least one membrane layer having a glass transition temperature, $T_g$, of the hard segment of greater than 212° F. (100° C.), preferably greater than 248° F. (120° C.).

U.S. Patent Application Ser. No. 60/836,423 filed on Aug. 8, 2006 and its corresponding U.S. Utility patent application Ser. No. 11/890,225 entitled "Chemically Cross-Linked Polymeric Membranes and Method of Use" which is herein incorporated by reference and Example 6 herein illustrates and provides an example of the low soft segment glass transition temperatures, $T_g$, that may be obtained and utilized in the polymeric membrane elements of the present invention.

Figure 9:
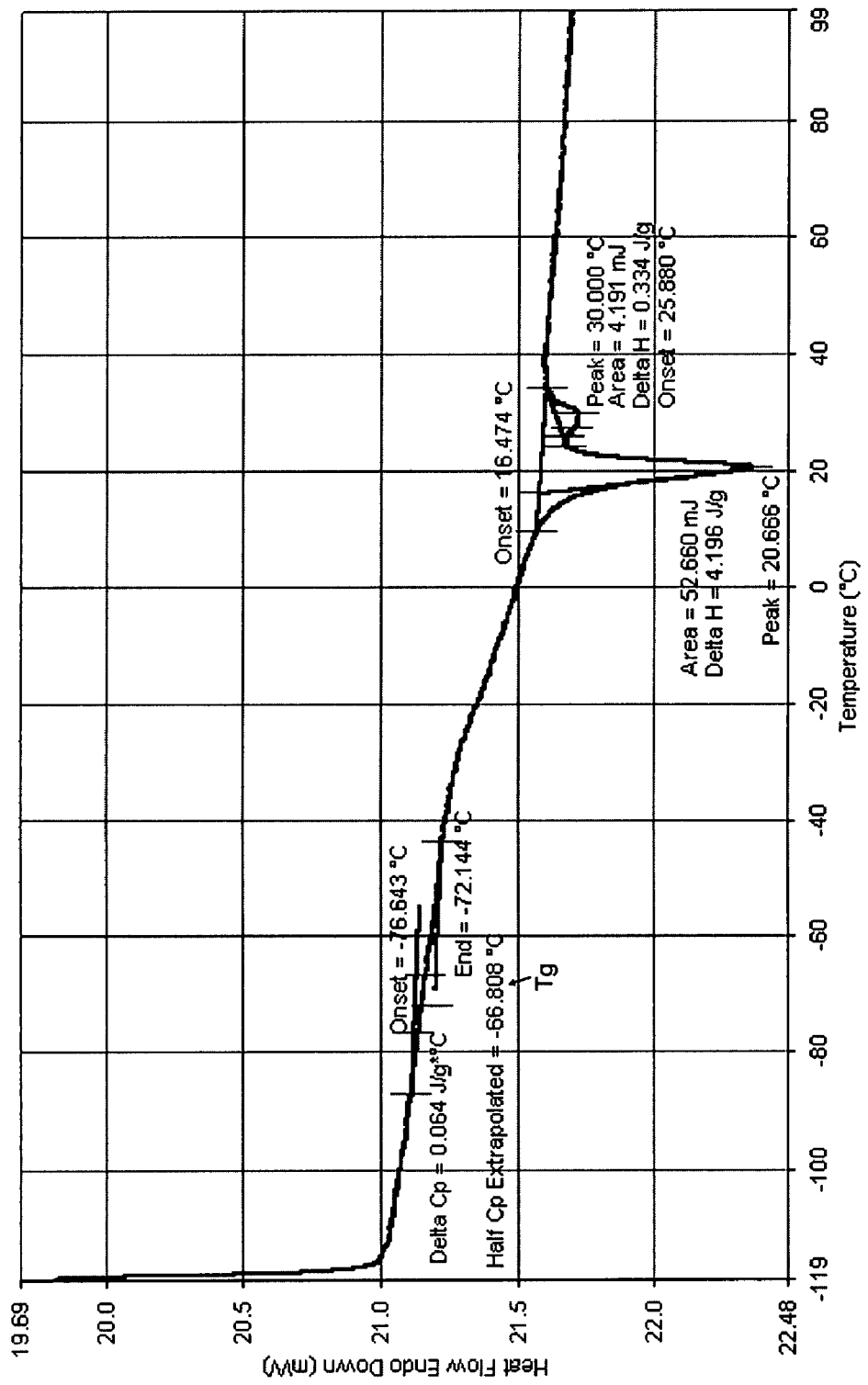
FIG. 9 is a graph of the heat flow vs. temperature testing of one embodiment of a membrane element composition of the present invention exhibiting a soft segment glass transition temperature, ($T_g$), of about −66.808° C.

FIG. 9 herein is one illustration of the low soft segment glass transition temperature, ($T_g$), that may be obtained in the polyimide polymer membrane layers of the present invention. The synthesis and fabrication of the PEA-DECO chemically cross-linked copolymer membrane possessing the $T_g$ as shown in FIG. 9 are presented in Example 6 herein. As can be seen in FIG. 9, the soft segment glass transition temperature, $T_g$, of the membrane was determined to be about $-66.808°$ C.

The relative concentration of the aromatic C-H components associated with a membrane element's hard segment and the concentration of the aliphatic C—H components associated with the membrane element's soft segment can be compared by determining the areas associated with each of these components in their Absorbance Infra-red Spectrum. The method for determining the Aliphatic C-H Area and the Aromatic C-H Area associated with the Absorbance Infra-red Spectrum of a membrane sample is further detailed in Example 6 herein. The areas defined by the Aliphatic C-H Area and the Aromatic C-H Area for a particular membrane sample provide a proportional measurement of the content of a membrane sample's soft and hard segments respectfully. While these areas should not be used to directly compare one membrane sample to another membrane sample, the ratio of the Aliphatic C-H Area to Aromatic C-H Area from one sample can be compared to the ratio of the Aliphatic C-H Area to Aromatic C-H Area of another sample to determine the relative soft to hard ratios in the final membranes. The determination of the value of the Aliphatic C-H Area and Aromatic C-H Area for a membrane sample as used herein is further illustrated and defined in Example 6 and associated FIGS. 11, 12, 13, and 14.

In an embodiment of the present invention, the Absorbance Infra-red Spectrum of at least membrane element has an Aliphatic C-H Area to Aromatic C-H Area ratio of at least 10. In a preferred embodiment, the Absorbance Infra-red Spectrum of at least membrane element has an Aliphatic C-H Area to Aromatic C-H Area ratio of at least 15, and even more preferably an Aliphatic C-H Area to Aromatic C-H Area ratio of least 20. In a most preferred embodiment, the Absorbance Infra-red Spectrum of at least membrane element has an Aliphatic C-H Area to Aromatic C-H Area ratio of at least 25. Since it is believed that the permeation performance of the membrane of the present invention is primarily attributable to the membrane soft segment, this increase in soft segment concentration results in improved separations performance properties for the membrane of the present invention.

Preferred cross-linking agents for use in the polymer membrane elements described above include, but are not limited to, diepoxycyclooctane, diepoxyoctane, 1,3-butadiene diepoxide, glycerol diglycidyl ether, bisphenol A diglycidyl ether, 1,4-butanediol diglycidyl ether, 1,4-cyclohexanedimethanol diglycidyl ether, bisphenol F diglycidyl ether, neopentyl glycol diglycidyl ether, poly(propylene glycol) diglycidyl ether, and mixtures thereof.

The polymeric films are particularly useful in the membrane assemblies of the present invention to modify the carbon weight shifting of the permeate product and may be particularly beneficial in the achieving the lower carbon weight cut-points in the permeate product. The porosity and characteristics of the polymeric film materials may be selected such that desired diffusion resistances, selectivities, or pressure drops are achieved to facilitate the boundary properties between or within membrane elements to effectuate the carbon weight selective diffusion across the overall membrane assembly. Preferred polymeric film materials, including, but not limited to, polytetrafluoroethylene (e.g., Teflon®), polyvinylidenefluoride (PVDF), polyvinylfluoride (PVF), aromatic polyamide fibers (e.g., Nomex® and Kevlar®), polyester, nylon, activated carbon fibers, latex, silicone, polyurethanes, polypropylenes, polyethylenes, polycarbonates, polysulfones, polyphenylene oxides, and combinations thereof can be utilized in the membrane assemblies of the present invention. In a more preferred embodiment, the polymeric films utilized in the membrane assembly of the present invention are selected from polytetrafluoroethylene, polyvinylidenefluoride, polyvinylfluoride, polyurethanes, polypropylenes, polyethylenes, polycarbonates, polysulfones, polyphenylene oxides, and combinations thereof. These polymeric films are particularly useful in the membrane assemblies of the present invention in achieving the carbon weight shift of the permeate product and may be particularly beneficial in the achieving the lower carbon weight cut-points in the permeate product.

The membrane assembly of the present invention present may be comprised of separate membrane elements and film elements. For example, an unsupported polymer membrane element may be incorporated as a separate element into the membrane assembly, and similarly, a polymer film may be incorporated as a separate element into the membrane assembly. The membranes and films may also be incorporated as joint elements in the membrane assembly of the present invention. These joint elements can include a film/membrane layer element (such as shown by the PEI/PTFE layer in FIG. 2), or a membrane layer/film/membrane layer element (such as shown by the PEI/PTFE/PEI layers in FIGS. 3 and 4), or alternatively a film/membrane layer/film element.

The membrane compositions and configurations of the present invention may be employed in separation processes that utilize a membrane in any workable housing configuration such as, but not limited to, flat plate elements, wafer cassette elements, spiral-wound elements, porous monoliths, porous tubes, or hollow fiber elements. Preferably, the assembly housing configuration employed is selected from flat plate elements, wafer cassette elements, spiral-wound elements, and porous monoliths. More preferably, the assembly housing configuration employed is selected from flat plate elements, wafer cassette elements, and spiral-wound elements.

The membrane compositions and configurations of the present invention can also be utilized in both unsupported and supported configurations. A non-limiting example of an unsupported membrane configuration includes casting the membrane layers onto a glass plate and subsequently removing it after the chemical cross-linking reaction is completed. Non-limiting examples of supported membrane configurations include casting the membrane onto a support material comprised of from materials such as, but not limited to, polytetrafluoroethylene (e.g., Teflon®), aromatic polyamide fibers (e.g., Nomex® and Kevlar®), porous metals, sintered metals, porous ceramics, polyester, nylon, activated carbon fibers, latex, silicone, permeable (porous) polymers including polyvinylfluoride, polyvinylidenefluoride, polyurethanes, polypropylenes, polyethylenes, polycarbonates, polysulfones, and polyphenylene oxides, metal and polymer foams (open-cell and closed-cell foams), silica, porous glass, mesh screens, and combinations thereof. Preferably, the polymeric membrane support is selected from polytetrafluoroethylene, aromatic polyamide fibers, porous metals, sintered metals, porous ceramics, polyester, nylon, activated carbon fibers, latex, silicone, permeable (porous) polymers including polyvinylfluoride, polyvinylidenefluoride, polyurethanes, polypropylenes, polyethylenes, polycarbonates, polysulfones, and polyphenylene oxides and combinations thereof.

In a preferred embodiment at least one polymeric membrane element of the membrane assembly is supported. A polymeric membrane element is considered supported if during the membrane fabrication process, the membrane copolymer solution is incorporated upon a support material. This differs from a polymeric film that is included in the membrane assembly, but is not utilized as a membrane element support material. While both the films utilized as a membrane support and those not utilized as a membrane support in the membrane assembly are counted in the total number of polymeric film layers in the assembly, only those that are used as a polymeric membrane support are considered as membrane supports. In a more preferred embodiment, at least two polymeric membrane elements of the membrane assembly are supported, and even more preferably, at least three polymeric membrane elements of the membrane assembly are supported.

The membrane assemblies of the present invention may be utilized in a pervaporation or a perstraction process configuration. The membrane assembly described herein is useful for separating a desired component or species from a liquid feed or a vapor/liquid feed. It is believed that both pressure dependent properties and non-pressure dependent properties of the membrane systems affect the final carbon weight distribution of the final product and that a combination of these process parameters can be tailored to result in the permeate product characteristics desired.

In addition to the membrane assemblies being utilized standalone in a process configuration, more than one of these membrane assemblies may be utilized in a single process application. These membrane assemblies may used in a series or parallel configuration, or any combination.

Figure 10:
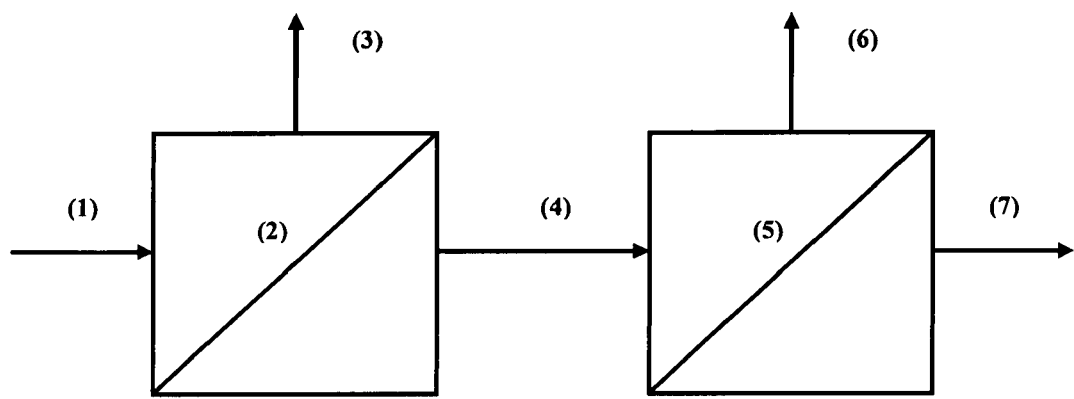
FIG. 10 is a schematic of a process configuration utilizing membrane assemblies of the present invention designed with different carbon weight cut-points in a two-stage process to produce a narrow carbon weight cut of an aromatic product.

In particular, it may be desired to use two membrane assemblies with different carbon weight cut-points in series to obtain a narrow intermediate carbon weight aromatic product. An example of such a two-stage narrow cut process separation configuration is shown in FIG. 10. Here, a hydrocarbon stream containing aromatics and non-aromatics (1) is fed to a first membrane assembly (2) which is designed with lower aromatic carbon weight cut-point than the second membrane assembly (5). As a non-limiting example, the first membrane assembly (2) could have an aromatic carbon weight cut-point in the range of $C_{7-}$ aromatic molecules and the second membrane assembly (5) could have an aromatic carbon weight cut-point in the range of $C_{8+}$ aromatic molecules. After contacting the first membrane assembly, most of the $C_7$ and lower carbon weight aromatics will not permeate through the membrane assembly and will be taken off with the first retentate stream (3). The first permeate stream (4), which is now rich in $C_8$ and higher aromatics, is routed to the second membrane assembly (5) with an aromatic carbon weight cut-point in the range of $C_{8-}$ aromatic molecules. Here, a large portion of the $C_9$ and heavier aromatic molecules will permeate through the membrane assembly to the second permeate stream (7) leaving behind a second retentate stream (6) which is high in concentration of a narrow range of aromatics on the order of $C_8$ molecules. The process described above is only one example of the capabilities of the present invention. The membrane assemblies of the present invention have the capabilities of being designed in conjunction with process conditions to make carbon weight cut-points at different carbon weight aromatics.

It should be noted that although carbon weight cut-points cannot be made with absolute precision, this invention can achieve carbon weight cut-point differentiations of over 100%, more often in the order of 1000%. Process results and analysis supporting this unique capability of the membrane assemblies of the present invention are shown in Examples 1-4 and in Table 1.

It should also be noted that the two-stage narrow cut process separation configuration shown in FIG. 10 and as described above can also be produced in a configuration wherein the first membrane has the higher aromatic carbon weight membrane assembly. Here, the first membrane assembly has a higher aromatic carbon weight cut-point than the second membrane assembly in the series and the first retentate is routed to a second membrane assembly with a lower aromatic carbon weight cut-point than the first membrane assembly. In this case, the narrow range carbon weight product would be produced in the second permeate instead of the second retentate from the second membrane assembly. The present invention also envisions processes utilizing more than two membrane separation stages and membrane permeate and retentate stream configurations that are apparent to those skilled in the art.

The membranes described herein are useful for separating a selected component or species from a liquid feed, a vapor/liquid feed, or a condensing vapor feeds. The resultant membranes of this invention can be utilized in both perstractive and pervaporative separation processes.

In a preferred embodiment, the permeate is removed from the permeate zone by a liquid or vapor sweep stream. The permeate dissolves into the sweep stream and is conducted away by sweep stream flow in order to prevent the accumulation of permeate in the permeate zone.

Membrane separation will preferentially operate at a temperature less than the temperature at which the membrane performance would deteriorate or the membrane would be physically damaged or decomposed. For hydrocarbon separations, the feedstream temperature would preferably range from about 32° F. to about 950° F. (0 to 510° C.), and more preferably from about 75° F. to about 500° F. (24 to 260° C.).

In a still another preferred embodiment, the operating pressure range in the retentate zone is from about atmospheric pressure to about 150 psig. The operating pressure ranges in the permeate zone is from about atmospheric pressure to about 1.0 mm Hg absolute.

The membranes of this invention are useful for separating a desired species or component from a feedstream, preferably a hydrocarbon feedstream.

In a preferred embodiment, the membrane compositions and configurations above are utilized for the selective separation of aromatics from a hydrocarbon feedstream containing aromatics and non-aromatics.

In another embodiment, the membrane compositions and configurations above are utilized to selectively separate sulfur and nitrogen heteroatoms from a hydrocarbon stream containing sulfur heteroatoms and nitrogen heteroatoms.

In still another embodiment, the hydrocarbon feedstream is a naphtha with a boiling range of about 80 to about 450° F. (27 to 232° C.), and contains aromatic and non-aromatic hydrocarbons. In a preferred embodiment, the aromatic hydrocarbons are separated from the naphtha feedstream. As used herein, the term naphtha includes thermally cracked naphtha, catalytically cracked naphtha, and straight-run naphtha. Naphtha obtained from fluid catalytic cracking processes ("FCC") are particularly preferred due to their high aromatic content.

Although the present invention has been described in terms of specific embodiments, it is not so limited. Suitable alterations and modifications for operation under specific conditions will be apparent to those skilled in the art. It is therefore intended that the following claims be interpreted as covering all such alterations and modifications as fall within the true spirit and scope of the invention.

EXAMPLES

In the following Examples 1 through 4, membrane assemblies designated as "Assembly A", "Assembly B", "Assembly C", and "Assembly D" were assembled as shown in FIGS. 1, 2, 3, and 4 respectively. The membranes were of a PEA/MOCA/DECO composition as disclosed in co-pending U.S. Patent Application Ser. No. 60/836,423 filed on Aug. 8, 2006 and its corresponding U.S. Utility patent application Ser. No. 11/890,225 entitled "Chemically Cross-Linked Polymeric Membranes and Method of Use" which is herein incorporated by reference as well as compositions disclosed herein and as further exemplified in Examples 5 and 6 herein.

Some of the membranes in the assemblies were single-layered (i.e., single polymer membrane layers) and the some of the membranes were integrally-layered (i.e., multiple polymer membrane layers) as designated in the configurations shown in FIGS. 1-4. The multi-layered membranes are also of a PEA/MOCA/DECO composition and the associated layering compositions and techniques are detailed in a concurrently filed, co-pending U.S. Patent Application Ser. No. 60/836,424 filed on Aug. 8, 2006 and its corresponding U.S. Utility patent application Ser. No. 11/890,224 entitled "Integrally-Layered Polymeric Membranes and Method of Use" which is herein incorporated by reference as well as membrane compositions disclosed herein and an example of the synthesis techniques for a integrally layered membrane as utilized in the present invention as illustrated in Example 7 herein.

The membrane coats in the membrane elements of Examples 1-4 ranged from about 3 to about 26 microns in thickness. The PTFE layers ranged from about 0.1 to about 0.3 micron pore size films that ranged from about 25 to about 88 microns in thickness.

Example 1

In this example, Assembly A was oriented in a membrane separation process where a heavy cat naphtha ("HCN") feedstream was subjected to the top face of the membrane assembly as shown in FIG. 1 and a permeate product was retrieved from the bottom side of the membrane assembly with respect to FIG. 1. The process conditions were run under pervaporation conditions at a feed pressure of approximately 100 psig, isothermal conditions of about a 284° F. (140° C.), and a permeate pressure of about 10 mm Hg.

Figure 5:
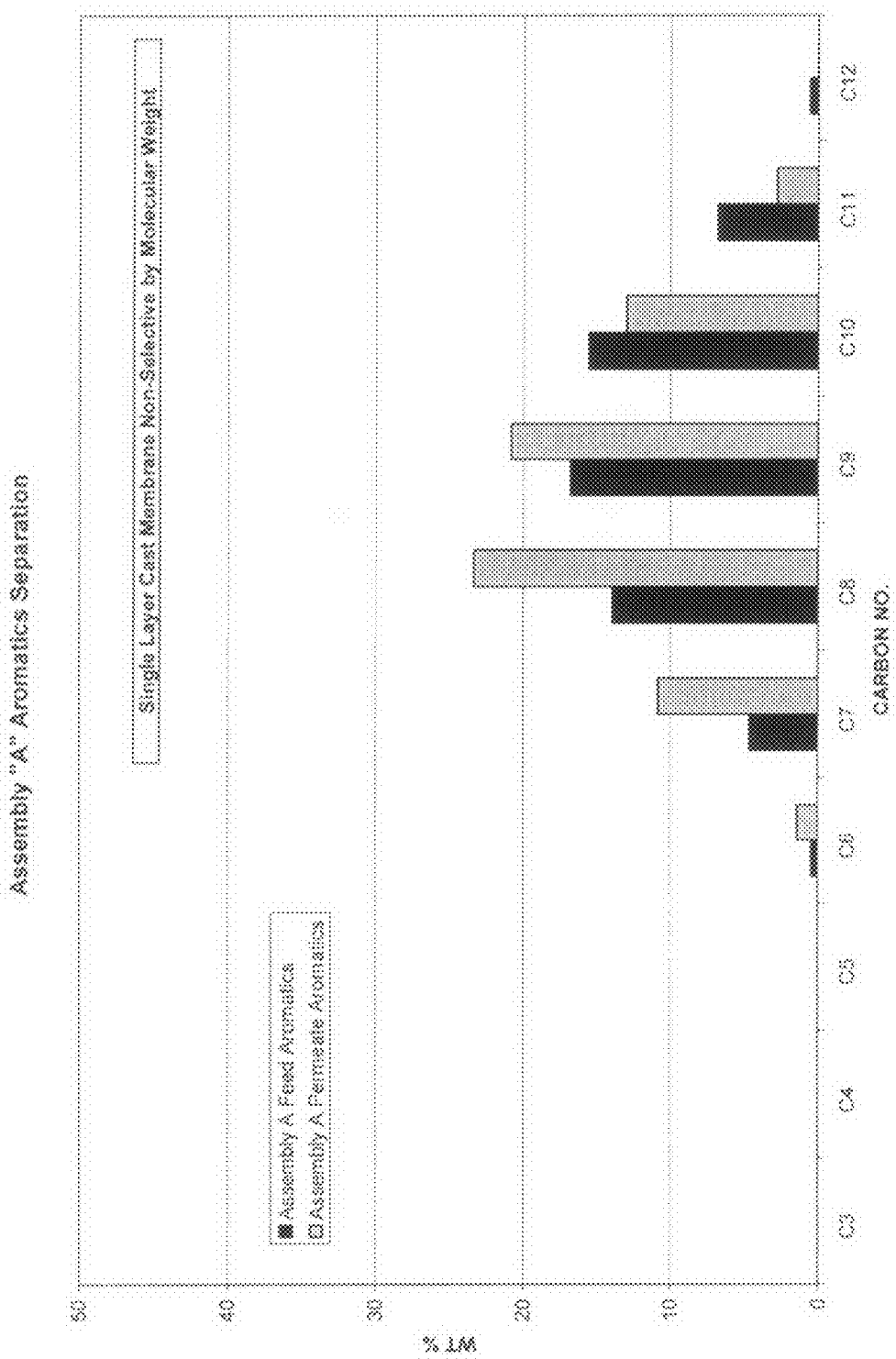
FIG. 5 is graph showing the process separation results of a single cast layer of a PEI membrane on PTFE (membrane "Assembly A") subject to a heavy cat naphtha feed.

Results of the aromatic permeate content versus the aromatic feed content are shown in FIG. 5. As can be seen in FIG. 5, the carbon weight distribution of the aromatics in the permeate generally follow the same carbon weight distribution of the aromatics in the feed. This example is utilized to demonstrate that there is little to no differentiation in the carbon weight distribution of the single layer cast polymeric membrane configurations of the prior art.

Example 2

In this example, Assembly B was oriented in a membrane separation a process where a heavy cat naphtha ("HCN") feedstream was subjected to the top face of the membrane assembly as shown in FIG. 2 and a permeate product was retrieved from the bottom side of the membrane assembly with respect to FIG. 2. The process conditions were run under pervaporation conditions at a feed pressure of approximately 75 to 100 psig, isothermal conditions of about a 284° F. (140° C.), and a permeate pressure of about 0 to 1.0 mm Hg.

Figure 6:
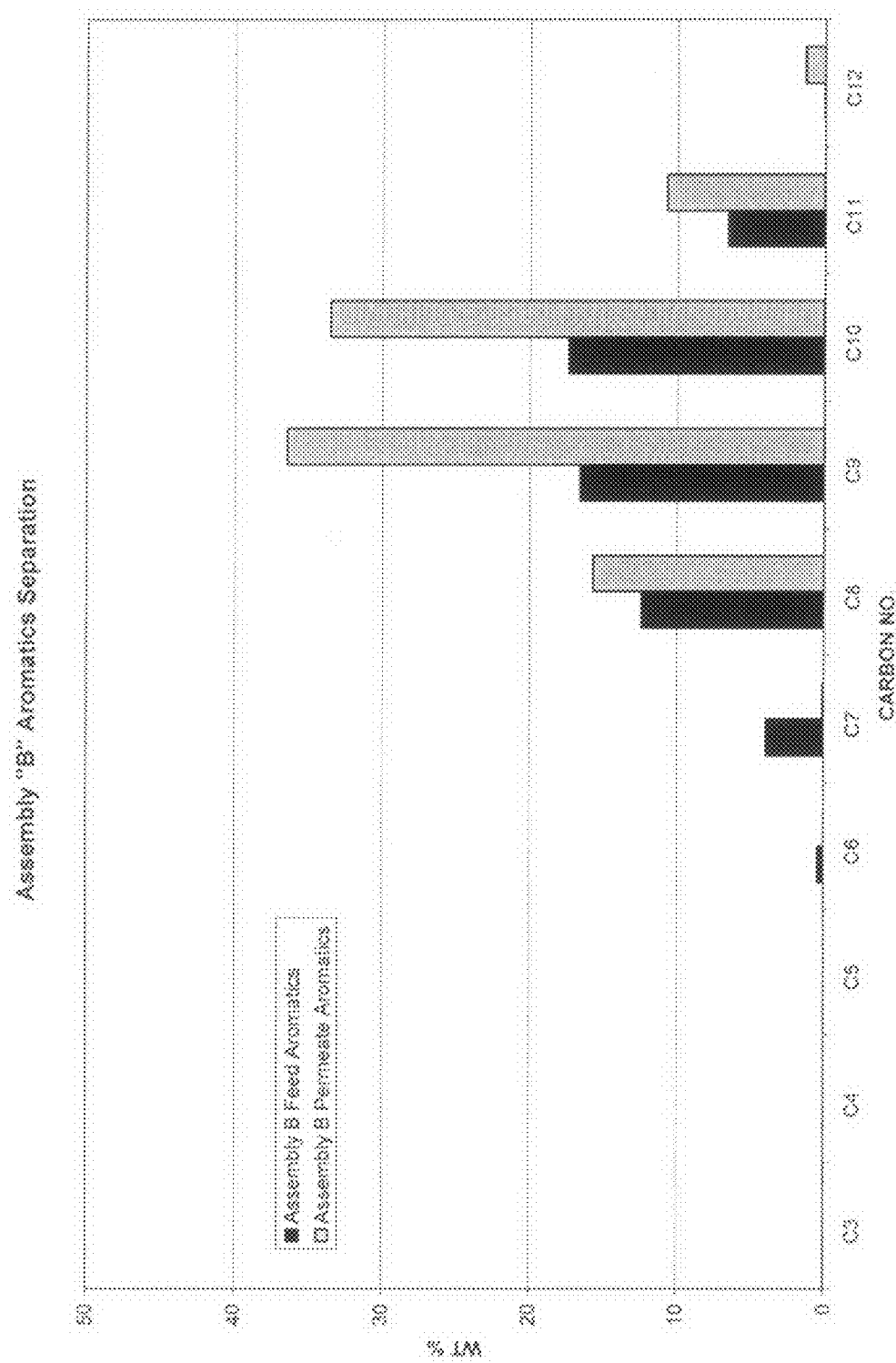
FIG. 6 is graph showing the process separation results of a cast layer of a PEI membrane on PTFE with a separate layer of PTFE film added to the PEI face (membrane "Assembly B") subject to a heavy cat naphtha feed.

Results of the aromatic permeate content versus the aromatic feed content are shown in FIG. 6. As can be seen in FIG. 6, the carbon weight distribution of the aromatics of the permeate was shifted to the higher carbon weights as compared to the carbon weight distribution of the aromatics in the feed. It can also be seen from FIG. 6 that nearly all of the $C_7$ and lower weight aromatics were excluded by the membrane assembly and therefore were not present in the permeate product.

Example 3

In this example, Assembly C was oriented in a membrane separation a process where a gasoline feedstream was subjected to the top face of the membrane assembly as shown in FIG. 3 and a permeate product was retrieved from the bottom side of the membrane assembly with as shown in FIG. 3. The process conditions were run under pervaporation conditions at a feed pressure of approximately 75 to 100 psig, isothermal conditions of about a 284° F. (140° C.), and a permeate pressure of about 0 to 1.0 mm Hg.

Results of the aromatic permeate content versus the aromatic feed content are shown in FIG. 7. As can be seen in FIG. 7, the carbon weight distribution of the aromatics of the permeate was shifted to the higher carbon weights as compared to the carbon weight distribution of the aromatics in the feed. It can also be seen from FIG. 2 that nearly all of the $C_7$ and lower weight aromatics were excluded by the membrane assembly and therefore were not present in the permeate product.

Example 4

In this example, Assembly D was oriented in a membrane separation a process where a gasoline feedstream, similar to the feedstream in Example 3, was subjected to the top face of the membrane assembly as shown in FIG. 4 and a permeate product was retrieved from the bottom side of the membrane assembly as shown in FIG. 4. The process conditions were run under pervaporation conditions at a feed pressure of approximately 75 to 100 psig, isothermal conditions of about a 284° F. (140° C.), and a permeate pressure of about 0 to 1.0 mm Hg.

Results of the aromatic permeate content versus the aromatic feed content are shown in FIG. 8. As can be seen in FIG. 8, the carbon weight distribution of the aromatics of the permeate was shifted to the higher carbon weights as compared to the carbon weight distribution of the aromatics in the feed. It can also be seen from FIG. 8 that the carbon weight cut-point shifted to around the $C_8$ aromatics as compared to Assembly C which had fewer layers and only had a carbon weight cut-point around the $C_7$ hydrocarbon molecules. The results of Example 8, as viewed in conjunction with the results from Example 7, clearly show that it is possible to modify the carbon weight distribution of the permeate as well as to design a shift in the carbon weight cut-point properties of the membrane assemblies of the present invention.

The process results from Examples 1 through 4 are shown in Table 1 below. As can be seen in the data for the single cast layer polymeric membrane assembly configuration of the prior art (Assembly A), the "Assembly A Permeate to Feed Ratio" decreased as the aromatic carbon weights increased. This shows that the single-layer membrane configuration is more selective toward the lower carbon weight aromatics in the feed.

The "% Increase from Preceding MW" values in Table 1 below are calculated by the following formula for each assembly:

TABLE 1

$$\frac{[\text{Permeate to Feed Ratio of } C_n] - [\text{Permeate to Feed Ratio of } C_{n-1}]}{[\text{Permeate to Feed Ratio of } C_{n-1}]} * 100$$

| | Carbon Weight of Aromatics | | | | | | | | | |
|---|---|---|---|---|---|---|---|---|---|---|
| | C3 | C4 | C5 | C6 | C7 | C8 | C9 | C10 | C11 | C12 |
| Assembly A Feed Aromatics (wt %) | 0 | 0 | 0 | 0.458 | 4.645 | 13.944 | 16.78 | 15.533 | 6.807 | 0.591 |
| Assembly A Permeate Aromatics (wt %) | 0 | 0 | 0 | 1.421 | 10.814 | 23.35 | 20.823 | 12.97 | 2.799 | 0.056 |
| Assembly A Permeate to Feed Ratio | N/A | N/A | N/A | 3.10 | 2.33 | 1.67 | 1.24 | 0.83 | 0.41 | 0.09 |
| % Increase from Preceeding MW | N/A | N/A | N/A | N/A | −24.96 | −28.07 | −25.89 | −32.71 | −50.75 | −76.96 |
| Assembly B Feed Aromatics (wt %) | 0 | 0 | 0 | 0.43 | 3.934 | 12.411 | 16.542 | 17.363 | 6.543 | 0.033 |
| Assembly B Permeate Aromatics (wt %) | 0 | 0 | 0 | 0 | 0.091 | 15.674 | 36.46 | 33.516 | 10.687 | 1.32 |
| Assembly B Permeate to Feed Ratio | N/A | N/A | N/A | 0.00 | 0.02 | 1.26 | 2.20 | 1.93 | 1.63 | 40.00 |
| % Increase from Preceeding MW | N/A | N/A | N/A | N/A | N/A | 5359.67 | 74.52 | −12.42 | −15.38 | 2348.96 |
| Assembly C Feed Aromatics (wt %) | 0 | 0 | 0 | 0.531 | 7.055 | 10.715 | 9.017 | 6.75 | 2.26 | 0.073 |
| Assembly C Permeate Aromatics (wt %) | 0 | 0 | 0 | 0 | 0.782 | 17.326 | 23.778 | 23.732 | 8.937 | 0.377 |
| Assembly C Permeate to Feed Ratio | N/A | N/A | N/A | 0.00 | 0.11 | 1.62 | 2.64 | 3.52 | 3.95 | 5.16 |
| % Increase from Preceeding MW | N/A | N/A | N/A | N/A | N/A | 1358.80 | 63.08 | 33.33 | 12.47 | 30.60 |
| Assembly D Feed Aromatics (wt %) | 0 | 0 | 0 | 0.531 | 7.055 | 10.715 | 9.017 | 6.75 | 2.26 | 0.073 |
| Assembly D Permeate Aromatics (wt %) | 0 | 0 | 0 | 0 | 0.045 | 0.18 | 2.793 | 57.309 | 23.238 | 0.065 |
| Assembly D Permeate to Feed Ratio | N/A | N/A | N/A | 0.00 | 0.01 | 0.02 | 0.31 | 8.49 | 10.28 | 0.89 |
| % Increase from Preceeding MW | N/A | N/A | N/A | N/A | N/A | 163.37 | 1743.86 | 2641.01 | 21.11 | −91.34 |

Comparing the process data obtained for Assembly A to the process data obtained for Assemblies B, C, and D in Table 1, it can be seen for the multi-layer membrane assemblies B, C, and D that the "% Increase from Preceding MW" is normally positive which shows that the multi-layer membrane assemblies of the present invention are more selective toward the higher carbon weight aromatics. This is in direct contrast to Assembly A, where the "% Increase from Preceding MW" are all negative values and all low absolute values which shows the prior art membrane configuration's non-selectivity to carbon weights (illustrated by the low absolute values) and even a slight selectivity toward the lower carbon weight aromatics (illustrated by the negative values).

It also can be seen when comparing the data for Assembly A with the data of Assemblies B, C, and D in Table 1, that in the "% Increase from Preceding MW" values, there is a large jump in the value of this number proceeding the "carbon molecular weight cut-point" of membrane Assemblies B, C, and D. This value is generally high (over 1000%) of the previous carbon molecular weight ratio showing a very sharp cut in the carbon weight cut-point differentiation of the membrane assemblies of the present invention. This large cut-point value is not seen in the values for Assembly A, and in fact, these values are negative for Assembly A. It can be seen from the "% Increase from Preceding MW" in Table 1 that the carbon weight cut-point was at the carbon weight below $C_8$ in Assembly B, at the carbon weight below $C_8$ in Assembly C, and at the carbon weight below $C_9$ in Assembly D.

It can also be seen from Table 1 that substantially no $C_7$ and lighter carbon weight materials present in the feed were present in the membrane permeate of Assemblies B & C. By the term "substantially" it is meant that the ratio of the weight % of aromatics in the feed to the weight % of aromatics in the permeate for carbon weight aromatics equal to and less than the referenced carbon molecular weight is less than one. This is illustrated in Table 1 wherein the "Permeate to Feed Ratios" in the $C_7$ column are 0.02 and 0.11 for Assemblies B and C, respectively. Accordingly, It can also be seen from Table 1 that substantially no $C_9$ and lighter carbon weight materials present in the feed were present in the membrane permeate of Assembly D (i.e., the "Assembly D Permeate to Feed Ratios" for $C_7$, $C_8$, and $C_9$ aromatics were all less than one). It is contemplated that a membrane assembly utilizing a number of layers greater than the Assembly C but less than Assembly D would achieve a separation with substantially no $C_8$ and lighter carbon weight materials present in the feed to be present in the membrane permeate.

Example 5

Synthesis and Fabrication of a Single-Layer PEA-DECO Chemically Cross-Linked Copolymer Membrane In the synthesis, 5 g (0.0025 moles) of polyethylene adipate (PEA) diol (2000 g/mole) was reacted with 1.09 g (0.005 moles) of pyromellitic dianhydride (PMDA) to make a prepolymer in the end-capping step (165° C. for 6.5 hours). To this solution was added 25 g of dimethylformamide (DMF). The temperature was allowed to decrease to 70° C. 0.67 g (0.0025 moles) of 4,4-methylene bis(2-chloroaniline) (MOCA) was subsequently added (dissolved in 5 g DMF). In the DMF solution, one mole of the prepolymer reacts with one mole of MOCA to make a copolymer containing polyamic acid hard segment and PEA soft segment in the chain-extension step. An additional 59.5 g of DMF was then added. Subsequently, 89.5 g acetone was added to prevent gelling. The resulting solution was then stirred for 1.5 hours at 70° C. The solution was then cooled to room temperature under continual stirring conditions. 1.4 g (0.005 moles) of diepoxycyclooctane was added to the copolymer-DMF solution.

The final solution was cast onto a porous support of 0.2 micron porous Gortex® Teflon® in a 457.5 cm² (70.9 in²) casting frame at a mass loading of approximately 0.00158 g/cm². The membrane casting was first dried at a suitable temperature (e.g., room temperature) to remove most of the solvent (i.e., solvent evaporation), and subsequently low-temperature cured to promote chemical cross-linking at 150° C. (302° F.) for 1.5 hours to promote the reaction of diepoxide with pendent carboxylic acid groups.

Example 6

Comparison of the PEA-DECO Chemically Cross-Linked Copolymer Membrane Composition as Utilized in the Integrally Layered Membranes of the Present Invention to the Membrane Composition of the Prior Art A PEA-DECO chemically cross-linked copolymer membrane of the present invention was synthesized and fabricated as follows:

In the synthesis, 5.0 g (0.0025 moles) of polyethylene adipate (PEA) diol (2000 g/mole) was reacted with 1.09 g (0.005 moles) of pyromellitic dianhydride (PMDA) to make a prepolymer in the end-capping step (165° C. for 7 hours). To this solution was added 25 g of dimethylformamide (DMF). The temperature was allowed to decrease to 70° C. A separately prepared solution of 0.67 g (0.0025 moles) of 4,4-methylene bis(2-chloroaniline) (MOCA) dissolved in 5 g DMF was subsequently added. The solution was stirred at 70° C. for 2.0 hours to prevent gelling. An additional 60 g of DMF and 90.5 g of acetone was added during this time period to prevent gelling. In the DMF/acetone solution, one mole of the prepolymer reacts with one mole of MOCA to make a copolymer containing polyamic acid hard segment and PEA soft segment in the chain-extension step. The solution temperature was allowed to drop to room temperature and 0.70 g (0.005 moles) of Diepoxycyclooctane (DECO) was added to the solution. The solution was stirred at room temperature for 30 minutes. The result was a 4 wt % polymer solution in 50% DMF/50% acetone. An additional 94 g of DMF and 94 g of acetone was added to achieve a 2 wt % polymer solution in 50% DMF/50% acetone.

The 2 wt % polymer solution was centrifuged for 5 minutes. The solution was cast onto a porous support of 0.2 micron porous Gore-Tex® Teflon® and the thickness was adjusted by the use of a knife gap setting of 31 mils. The DMF and acetone was allowed to evaporate at room temperature. The membrane casting was first dried at a suitable temperature (e.g., room temperature) to remove most of the solvent (i.e., solvent evaporation), and subsequently low-temperature cured to promote chemical cross-linking at 180° C. (356° F.) for a minimum cure time of approximately 2.0 hours to promote the reaction of diepoxide with pendent carboxylic acid groups. The final curing step converts the polyamide ester hard segment to the polyimide hard segment via the imide ring closure.

A Diepoxycyclooctane PEI membrane of the prior art was synthesized and fabricated as follows:

In the synthesis, 5.0 g (0.0025 moles) of polyethylene adipate (PEA) diol (2000 g/mole) was reacted with 1.09 g (0.005 moles) of pyromellitic dianhydride (PMDA) to make a prepolymer in the end-capping step (165° C. for 7 hours). To this solution was added 25 g of dimethylformamide (DMF). The temperature was allowed to decrease to 70° C. A separately prepared solution of 0.67 g (0.0025 moles) of 4,4-methylene bis(2-chloroaniline) (MOCA) dissolved in 5 g DMF was subsequently added. The solution was stirred at 70° C. for 2.0 hours to prevent gelling. An additional 60 g of DMF and 90.5 g of acetone was added during this time period to prevent gelling. In the DMF/acetone solution, one mole of the prepolymer reacts with one mole of MOCA to make a copolymer containing polyamic acid hard segment and PEA soft segment in the chain-extension step. The solution temperature was allowed to drop to room temperature and 0.70 g (0.005 moles) of Diepoxycyclooctane (DECO) was added to the solution. The solution was stirred at room temperature for 30 minutes. The result was a 4 wt % polymer solution in 50% DMF/50% acetone. An additional 94 g of DMF and 94 g of acetone was added to achieve a 2 wt % polymer solution in 50% DMF/50% acetone.

The 2 wt % polymer solution was centrifuged for 5 minutes. The solution was cast onto a porous support of 0.2 micron porous Gore-Tex® Teflon® and the thickness was adjusted by the use of a knife gap setting of 31 mils. In the initial drying step, the DMF and acetone were evaporated from the membrane in a box purged with nitrogen gas at room temperature for approximately 6 hours. The membrane was then dried in an oven at 120° C. (248° F.), for about 24 hours. Finally, the membrane was cured at elevated-temperature to promote chemical cross-linking by heating from room temperature to 310° C. (590° F.), maintaining it at this temperature for 144 minutes to promote the reaction of diepoxide with pendent carboxylic acid groups and then cooling it to room temperature. The curing step converts the polyamide ester hard segment to the polyimide hard segment via the imide ring closure.

The Diepoxycyclooctane PEI membrane of the prior art above was made to represent the prior art membranes of U.S. Pat. Nos. 5,550,199 and 5,670,052. Both patents allow diamines to be selected from a group of diamine compounds. For the preparation of these membrane films, 4,4-methylene bis(2-chloroaniline) (MOCA) is used instead of methylene dianiline (MDA). The use of a halogenated diamine compound containing chlorine provides additional analytical capability in analyzing the membrane films. The chlorine atoms contained in the 4,4-methylene bis(2-chloroaniline) (MOCA) can be identified and detected by SIMS and SEM analytical methods. The synthesis methods used were adjusted to reflect the use of 4,4-methylene bis(2-chloroaniline) instead of the methylene dianiline (MDA) used in the examples disclosed in U.S. Pat. Nos. 5,550,199 and 5,670,052. It is believed that the membrane as formulated is an accurate simulation of the membranes of the prior art.

The use of a halogenated diamine compound containing chlorine (such as MOCA) provides additional analytical capability in analyzing the membrane films. The chlorine atoms are a potential tracer compound that is contained in the membrane film that can be analyzed for using a range of analytical methods known to those skilled in the art. This provides a convenient method for distinguishing between different membrane films created by different methods. This additional analytical characterization of membrane films is significantly more complex if compounds like methylene dianiline (MDA) are used in the preparation of the membrane films.

Each of the two as fabricated membranes above were subjected to Infra-red (IR) Reflectance Spectrum analysis and the results obtained were then converted to an Absorbance Spectrum using the Kubelka Monk transformation. The Absorbance Spectrum format provides a basis for comparison of the membrane characteristics since the band intensities (absorbance) and integrated areas obtained are proportional to the concentrations of the structural components.

Figure 11:
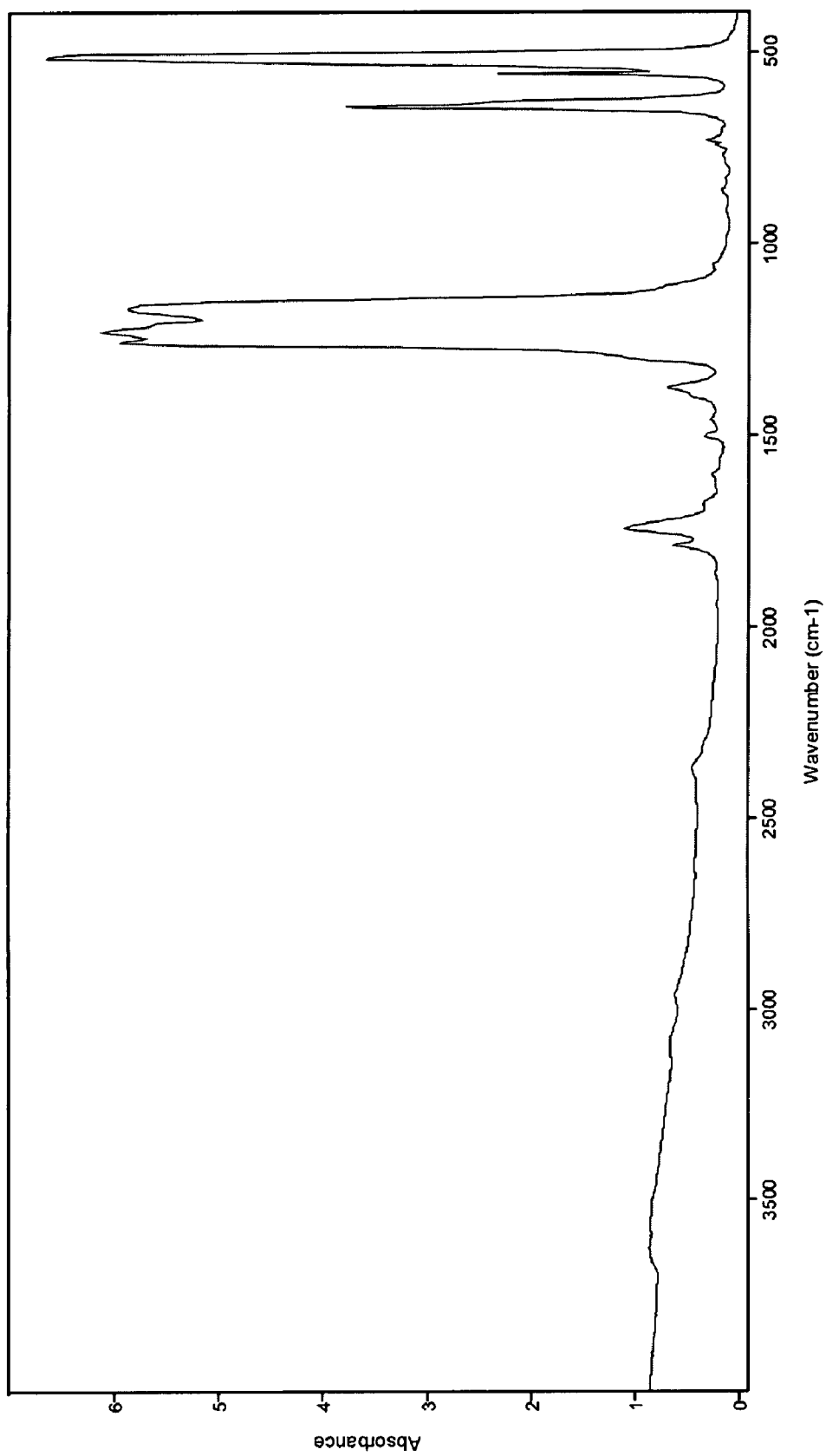
FIG. 11 is the Absorbance Infra-red Spectrum of the prior art membrane composition from Example 6.

The Absorbance Spectrum shown in FIG. 11 corresponds to the Diepoxycyclooctane PEI membrane of the prior art. The Absorbance Spectrum shown in FIG. 12 corresponds to the PEA-DECO chemically cross-linked copolymer membrane which may be used in the membrane layers of the present invention.

Figure 12:
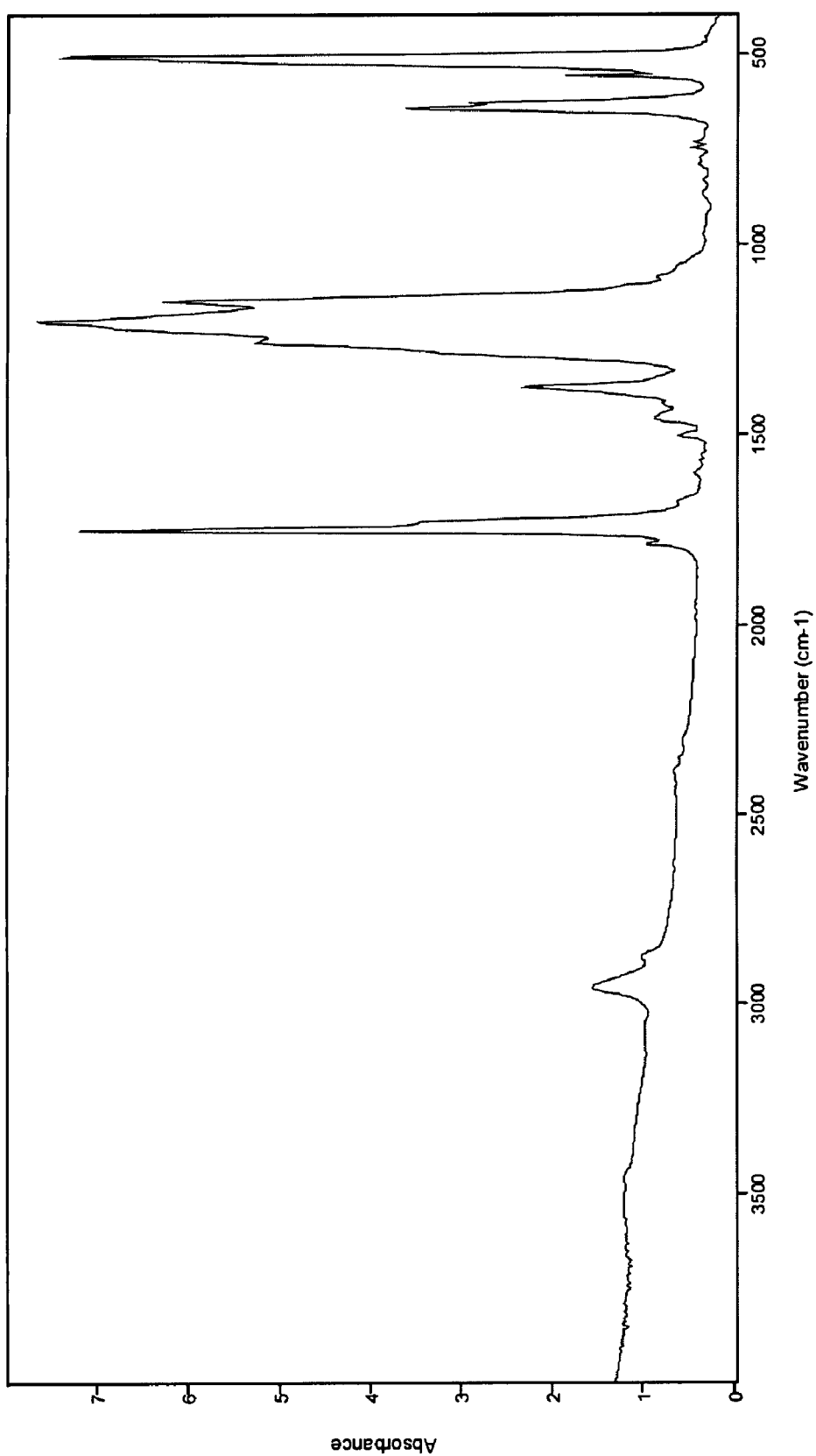
FIG. 12 is the Absorbance Infra-red Spectrum of one embodiment of a membrane layer composition of the present invention from Example 6.

As can be seen comparing FIGS. 11 and 12, significant differences can be seen in the absorbance values corresponding to the wavenumber values of about 3150 to about 2800 $cm^{-1}$, as well as the wavenumber values of 1875 to 1625 cm$^{-1}$. It should be pointed out that in the Absorbance Spectrum data, that values below about 2.0 are highly linear with respect to concentration and can be used for relative compositional comparison of molecular content within a membrane sample.

Figure 13:
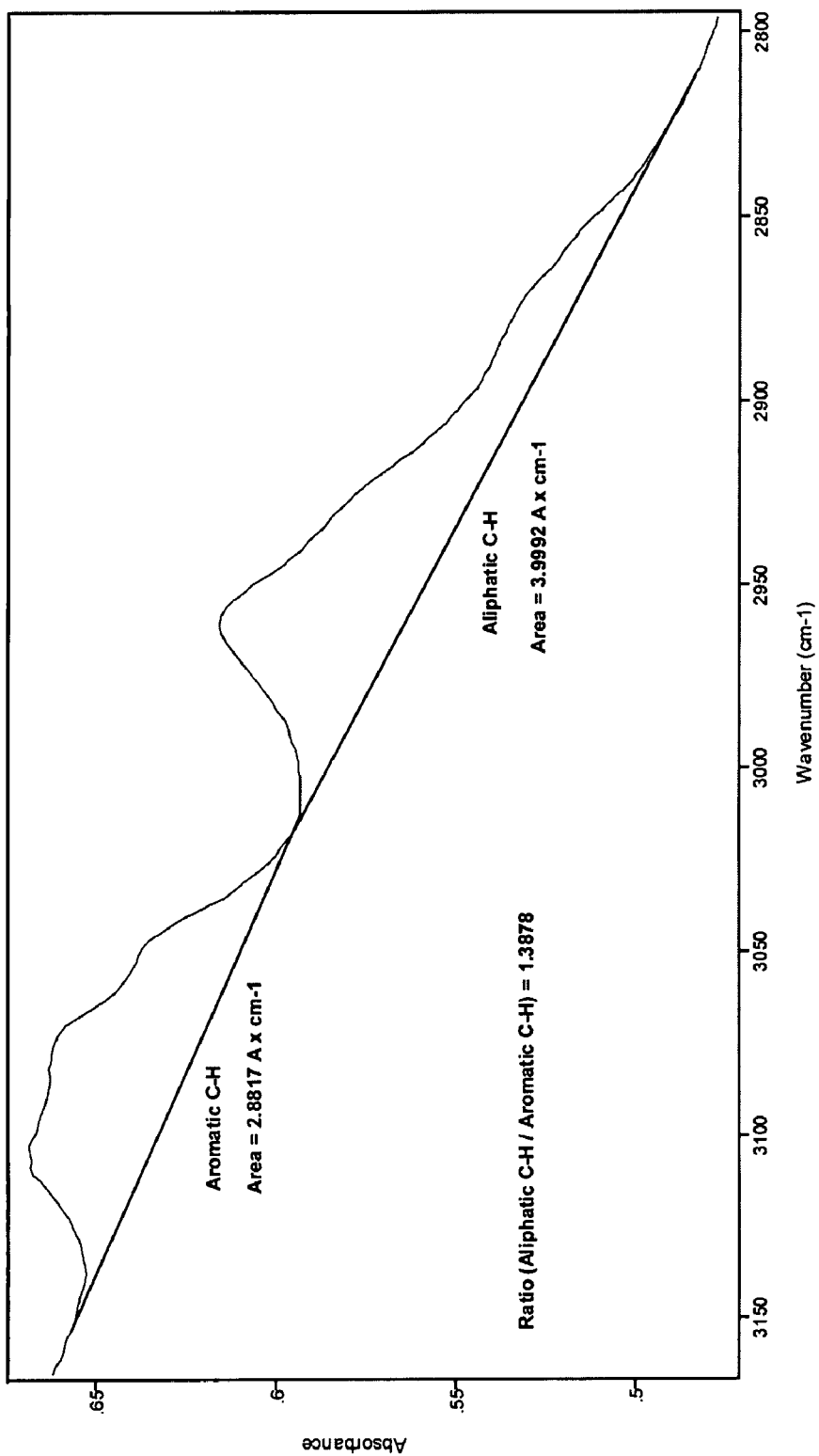
FIG. 13 is an expanded view of the Absorbance Infra-red Spectrum of FIG. 3 corresponding to wavenumbers of about 3150 to 2800 cm$^{-1}$, also showing the Aromatic C-H Area and the Aliphatic C-H Area for the prior art membrane composition from Example 6.

FIG. 13 shows an expanded sectional view of the absorbance values corresponding to wavenumber values of about 3150 to 2800 cm$^{-1}$ from FIG. 11 for the Diepoxycyclooctane PEI membrane of the prior art. Similarly, FIG. 14 shows an expanded sectional view of the absorbance values corresponding to wavenumber values of about 3150 to 2800 cm$^{-1}$ from FIG. 12 for the PEA-DECO chemically cross-linked copolymer membrane.

Figure 14:
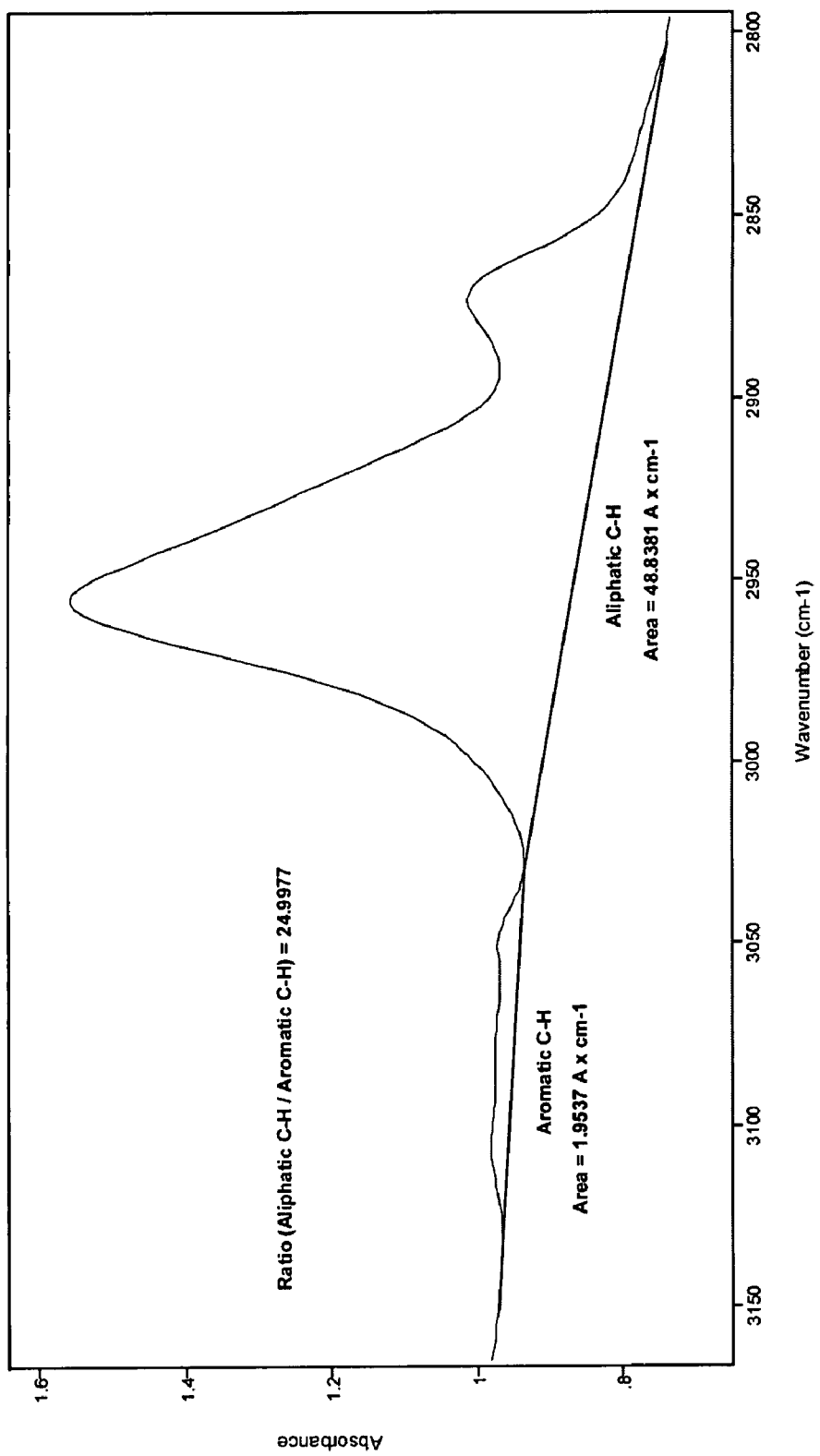
FIG. 14 is an expanded view of the Absorbance Infra-red Spectrum of FIG. 4 corresponding to wavenumbers of about 3150 to 2800 cm$^{-1}$, also showing the Aromatic C-H Area and the Aliphatic C-H Area for one embodiment of a membrane layer composition of the present invention from Example 6.

In FIGS. 13 and 14, in order to evaluate the relative concentration of the aromatic C-H components associated with the membrane's hard segment and the concentration of the aliphatic C-H components associated with the membrane's soft segment peaked the area defined by the absorbance value curve and a "baseline" must be determined for the particular component. The baseline for the aromatic C-H components is determined by a straight line drawn between the two minima on either side of the aromatic C-H component absorbance peak. In FIGS. 13 and 14, these two minima are at approximately 3150 and 3025 cm$^{-1}$, respectively. The area defined by the integrated area between the absorbance values and the baseline between the two minima defines the Aromatic C-H Area. This Aromatic C-H Area is proportional to the hard segment content of the final polymer membrane.

In a similar manner, the baseline for the aliphatic C-H components is determined by a straight line drawn between the two minima on either side of the aliphatic C-H component absorbance peak. In FIGS. 13 and 14, these two minima are at approximately 3025 and 2800 cm$^{-1}$, respectively. The area defined by the integrated area between the absorbance values and the baseline between the two minima defines the Aliphatic C-H Area. This Aliphatic C-H Area is proportional to the soft segment content of the final polymer membrane. The determination of the value of the Aliphatic C-H Area and Aromatic C-H Area for membrane sample as utilized herein is defined by this procedure.

Comparing these areas for the Diepoxycyclooctane PEI membrane of the prior art (FIG. 13) and the PEA-DECO chemically cross-linked copolymer membrane of the present invention (FIG. 14), it can be seen that the PEA-DECO chemically cross-linked copolymer membrane of the present invention in FIG. 14 shows a significant peak in the absorbance values corresponding to wavenumber values of about 3025 to about 2800 cm$^{-1}$ as compared with the same values in the prior art membrane shown in FIG. 13. This shows that the membrane of the present invention possess a significantly higher ratio of the aliphatic C-H soft segment as compared to the aromatic C-H hard segment.

While the absolute areas nor the absolute absorbance values between FIG. 13 and FIG. 14 should not be compared directly, the Aliphatic C-H Area/Aromatic C-H Area ratio (also referred to herein as the "Aliphatic C-H Area to Aromatic C-H Area ratio") for a given membrane is an accurate measurement of the relative concentrations of the Aromatic C-H components and the Aliphatic C-H components of the membrane. Therefore, the ratio of these areas is a suitable measurement for direct comparison of two different polymer membrane specimens. As can be seen comparing FIGS. 13 and 14, the Ratio of Aliphatic C—H Area/Aromatic C-H Area of the Infra-red Absorbance Spectrum is about 1.39 for the Diepoxycyclooctane PEI membrane of the prior art. In contrast, the Ratio of Aliphatic C-H Area/Aromatic C-H Area of the Infra-red Absorbance Spectrum is about 25.00 for the PEA-DECO chemically cross-linked copolymer membrane of the present invention.

Example 7

Synthesis and Fabrication of a Integrally Layered PEA-DECO Chemically Cross-Linked Copolymer Membrane In this example, a PEA-DECO polymer solution was prepared in the same manner as Example 5 above. The final solution was cast in a first membrane layer onto a porous support of 0.2 micron porous Gortex® Teflon® in a 9.5" (24.13 cm) diameter casting frame at a mass loading of approximately 0.00129 g/cm$^2$. The first layer of the membrane casting was dried at approximately 100° C. for about 10 minutes to remove most of the solvent (i.e., solvent evaporation). The solution was then cast onto the first membrane layer at a mass loading of approximately 0.00133 g/cm$^2$ to form a second membrane layer. The integrated membrane layers were subsequently low-temperature cured at 150° C. (302° F.) for 1.5 hours to promote chemical cross-linking reactions internal to and at the interface of the first and second membrane layers to form an integrally-layered polyimide membrane.

Similarly, more than two integral layers can be incorporated into a single membrane element by repeating the steps above for each incorporated layer prior to final curing. In this manner multi-layered integrally-layered membrane elements can be fabricated.

What is claimed is:

1. A process for separating aromatics from a hydrocarbon feedstream containing aromatics and non-aromatics comprising:

a) contacting one side of a membrane assembly with a hydrocarbon steam, wherein the membrane assembly is comprised at least two polymeric membrane elements and at least two polymer films, wherein a retentate stream and a permeate stream are extracted from the membrane assembly, and wherein at least one polymeric membrane element is comprised of a dianhydride, a diamine, a cross-linking agent and a difunctional dihydroxy polymer selected from:
   i) dihydroxy end-functionalized ethylene propylene copolymers with an ethylene content from about 25 wt % to about 80 wt %;
   ii) dihydroxy end-functionalized ethylene propylene diene terpolymers with an ethylene content from about 25 wt % to about 80 wt %;
   iii) dihydroxy end-functionalized polyisoprenes; dihydroxy end-functionalized polybutadienes; dihydroxy end-functionalized polyisobutylenes;
   iv) dihydroxy end-functionalized acrylate homopolymers, copolymers and terpolymers; dihydroxy end-functionalized methacrylate homopolymers, copolymers and terpolymers; and mixtures thereof, wherein the mixtures of acrylate and methacrylate monomers range from $C_1$ to $C_{18}$;
   v) dihydroxy end-functionalized condensation homopolymers, copolymers, terpolymers and higher order compositions of structurally different monomers, including alcohol-terminated end-functionalized esters and dihydroxy end-functionalized multi-monomer polyesters; and mixtures thereof, wherein the polyalkyladipate structures range from $C_1$ to $C_{18}$;
   vi) dihydroxy end-functionalized perfluoroelastomers;

vii) dihydroxy end-functionalized urethane homopolymers, copolymers, terpolymers, and higher order compositions of structurally different monomers;

viii) dihydroxy end-functionalized carbonate homopolymers, copolymers, terpolymers, and higher order compositions of structurally different monomers;

ix) dihydroxy end-functionalized ethylene alpha-olefin copolymers; dihydroxy end-functionalized propylene alpha-olefin copolymers; and dihydroxy end-functionalized ethylene propylene alpha-olefin terpolymers, wherein the alpha-olefins are linear or branched and range from C3 to C18;

x) dihydroxy end-functionalized styrene homopolymers, copolymers, terpolymers, and higher order compositions of structurally different monomers;

xi) dihydroxy end-functionalized silicone homopolymers, copolymers, terpolymers, and higher order compositions of structurally different monomers;

xii) dihydroxy end-functionalized styrene butadiene copolymers; dihydroxy end-functionalized styrene isoprene copolymers; and xiii) dihydroxy end-functionalized styrene butadiene block copolymers; and dihydroxy end-functionalized styrene isoprene block copolymers; and b) extracting a permeate stream from the opposite side of the membrane assembly, wherein the weighted average of the carbon weights of the aromatics in the permeate stream is at least one carbon weight higher than the weighted average of the carbon weights of the aromatics in the feedstream, wherein the membrane assembly is composed of a top layer of polymer film, a bottom layer of polymer film, and from 2 to 6 polymeric membrane elements disposed therebetween, and wherein each polymeric membrane element is comprised of a middle layer of a porous polytetrafluoroethylene film having a pore size from about 0.1 to about 0.3 microns surrounded on to and bottom with cast polymer layers comprised of the reaction product of the dianhydride, diamine, cross-linking agent, and difunctional dihydroxy polymer.

2. The process of claim 1, wherein the weighted average of the carbon weights of the aromatics in the permeate stream is at least two carbon weights higher than the weighted average of the carbon weights of the aromatics in the feedstream.

3. The process of claim 1, wherein the top and bottom polymer layers are each comprised of a hard segment and a soft segment, each soft segment having a glass transition temperature, $T_g$, of less than 77° F. (25° C.).

4. The process of claim 3, wherein the crosslinking agent is selected from diepoxycyclooctane, diepoxyoctane, 1,3-butadiene diepoxide, glycerol diglycidyl ether, bisphenol A diglycidyl ether, 1,4-butanediol diglycidyl ether, 1,4-cyclohexanedimethanol diglycidyl ether, bisphenol F diglycidyl ether, neopentyl glycol diglycidyl ether, poly(propylene glycol) diglycidyl ether, and mixtures thereof.

5. The process of claim 4, wherein at least one polymer film is comprised of a material selected from polytetrafluoroethylene, polyvinylidenefluoride, polyvinylfluoride, aromatic polyamide fiber, polyester, nylon, activated carbon fiber, latex, silicone, polyurethane, polypropylene, polyethylene, polycarbonate, polysulfone, polyphenylene oxide, and combinations thereof.

6. The process of claim 5, wherein at least one polymeric membrane element is incorporated onto a membrane support material selected from polytetrafluoroethylene, aromatic polyamide fiber, porous metal, sintered metal, porous ceramic, polyester, nylon, activated carbon fiber, latex, silicone, polyvinylfluoride, polyvinylidenefluoride, polyurethane, polypropylene, polyethylene, polycarbonate, polysulfone, polyphenylene oxide, metal foam, polymer foam, silica, porous glass, mesh screen, and combinations thereof.

7. The process of claim 3, wherein at least one polymeric membrane element of the membrane assembly exhibits an Absorbance Infra-red Spectrum having an Aliphatic C-H Area to Aromatic C-H Area ratio of at least 10.

8. The process of claim 3, wherein the process is operated under pervaporation conditions, the hydrocarbon feedstream is comprised of $C_7$ to $C_{12}$ aromatics and non-aromatics, and the $C_8$ permeate aromatic wt %:$C_8$ feed aromatic wt % ratio is at least 100% greater than the $C_7$ permeate aromatic wt %:$C_7$ feed aromatic wt % ratio.

9. The process of claim 3, wherein the process is operated under pervaporation conditions, the hydrocarbon feedstream is comprised of $C_7$ to $C_{12}$ aromatics and non-aromatics, and the $C_9$ permeate aromatic wt %:$C_9$ feed aromatic wt % ratio is at least 100% greater than the $C_8$ permeate aromatic wt %:$C_8$ feed aromatic wt % ratio.

10. The process of claim 3, wherein the process is operated under pervaporation conditions, the hydrocarbon feedstream is comprised of $C_7$ to $C_{12}$ aromatics and non-aromatics, and the $C_{10}$ permeate aromatic wt %:$C_{10}$ feed aromatic wt % ratio is at least 100% greater than the $C_9$ permeate aromatic wt %:$C_9$ feed aromatic wt % ratio.

11. The process of claim 3, wherein the process is operated under pervaporation conditions, the hydrocarbon feedstream is comprised of $C_7$ to $C_{12}$ aromatics and non-aromatics, and at least one $C_{n+1}$ permeate aromatic wt %:$C_{n+1}$ feed aromatic wt % ratio is at least 100% greater than the $C_n$ permeate aromatic wt %:feed aromatic wt % ratio.

12. The process of claim 11, wherein each at least one polymeric membrane element is comprised of a dianhydride, a diamine, a cross-linking agent and a difunctional dihydroxy polymer selected from:

a) dihydroxy end-functionalized condensation homopolymers, copolymers, terpolymers and higher order compositions of structurally different monomers, including alcohol-terminated end-functionalized esters and dihydroxy end-functionalized multimonomer polyesters, and mixtures thereof, wherein the polyalkyladipate structures range from $C_1$ to $C_{18}$;

b) dihydroxy end-functionalized perfluoroelastomers;

c) dihydroxy end-functionalized carbonate homopolymers, copolymers, terpolymers, and higher order compositions of structurally different monomers; and d) dihydroxy end-functionalized ethylene alpha-olefin copolymers; dihydroxy end-functionalized propylene alpha-olefin copolymers; and dihydroxy end-functionalized ethylene propylene alpha-olefin terpolymers, wherein the alpha-olefins are linear or branched and range from C3 to C18.

13. The process of claim 12, wherein the Absorbance Infrared Spectrum of at least one polymeric membrane element of the membrane assembly has an Aliphatic C—H Area to Aromatic C-H Area ratio of at least 10 and the polymeric membrane has a soft segment glass transition temperature, $T_a$, of less than 32° F. (0° C.).

14. The process of claim 13, wherein the process is operated under pervaporation conditions, the hydrocarbon feedstream is comprised of $C_7$ to $C_{12}$ aromatics and non-aromatics, and at least one $C_{n+1}$ permeate aromatic wt %:$C_{n+1}$ feed aromatic wt % ratio is at least 1000% greater than the $C_n$ permeate aromatic wt %:$C_n$ feed aromatic wt % ratio.

15. The process of claim 14, wherein the hydrocarbon feedstream is a naphtha with a boiling range of about 80 to about 450° F. (27 to 232° C.), and contains aromatic and non-aromatic hydrocarbons.

16. The process of claim 15, wherein feedstream temperature is from about 75° F. to about 500° F. (24 to 260° C.) and the pressure in the retentate zone is from about atmospheric pressure to about 150 psig.

17. A process for separating aromatics from a hydrocarbon feedstream containing aromatics and non-aromatics comprising:
  a) contacting a first polymeric membrane assembly with a first carbon weight aromatic cut-point, resulting in a first retentate and a first permeate; and
  b) contacting the first permeate with a second polymeric membrane assembly with a second carbon weight aromatic cut-point, wherein the second carbon weight aromatic cut-point that is higher than the first carbon weight aromatic cut-point of the first polymeric membrane assembly, resulting in a second retentate and a second permeate, wherein no more than two consecutive carbon weight aromatics comprise at least 75 wt % of the total aromatics in the second retentate, and wherein the combined wt % of the two consecutive carbon weight aromatics in said second retentate is at least 100% greater than the combined wt % of the two consecutive carbon weight aromatics in the hydrocarbon feedstream and
wherein the first and second membrane assemblies are each composed of a top layer of polymer film, a bottom layer of polymer film, and from 2 to 6 polymeric membrane elements disposed therebetween, and wherein each polymeric membrane element is comprised of a middle layer of a porous polytetrafluoroethylene film having a core size from about 0.1 to about 0.3 microns surrounded on top and bottom with cast polymer layers comprised of a dianhydride, a diamine, a cross-linking agent and a difunctional dihydroxy polymer selected from:
  a) dihydroxy end-functionalized ethylene propylene copolymers with an ethylene content from about 25 wt % to about 80 wt %;
  b) dihydroxy end-functionalized ethylene propylene diem terpolymers with an ethylene content from about 25 wt % to about 80 wt %;
  c) dihydroxy end-functionalized polyisoprenes: dihydroxy end-functionalized polybutadienes: dihydroxy end-functionalized polyisobutylenes;
  d) dihydroxy end-functionalized acrylate homopolymers, copolymers and terpolymers; dihydroxy end-functionalized methacrylate homopolymers, copolymers and terpolymers; and mixtures thereof, wherein the mixtures of acrylate and methacrylate monomers range from C1 to C18;
  e) dihydroxy end-functionalized condensation homopolymers, copolymers, terpolymers and higher order compositions of structurally different monomers, including alcohol-terminated end-functionalized esters and dihydroxy end-functionalized multimonomer polyesters; and mixtures thereof, wherein the polyalkyladipate structures range from C1 to C18;
  f) dihydroxy end-functionalized perfluoroelastomers;
  g) dihydroxy end-functionalized urethane homopolymers, copolymers, terpolymers, and higher order compositions of structurally different monomers;
  h) dihydroxy end-functionalized carbonate homopolymers, copolymers, terpolymers, and higher order compositions of structurally different monomers;
  i) dihydroxy end-functionalized ethylene alpha-olefin copolymers; dihydroxy end-functionalized propylene alpha-olefin copolymers; and dihydroxy end-functionalized ethylene propylene alpha-olefin terpolymers; wherein the alpha-olefins arc linear or branched and range from $C_3$ to $C_{18}$;
  j) dihydroxy end-functionalized styrene homopolymers, copolymers, terpolymers, and higher order compositions of structurally different monomers;
  k) dihydroxy end-functionalized silicone homopolymers, copolymers, terpolymers, and higher order compositions of structurally different monomers;
  l) dihydroxy end-functionalized styrene butadiene copolymers; dihydroxy end-functionalized styrene isoprene copolymers; and
  m) dihydroxy end-functionalized styrene butadiene block copolymers; and dihydroxy end-functionalized styrene isoprene block copolymers.

18. The process of claim 17, wherein each at least one polymeric membrane element of the membrane assembly is comprised of a hard segment and a soft segment, wherein the soft segment has a glass transition temperature, $T_g$ of less than 77° F. (25° C.), and wherein the at least one polymeric membrane element exhibits an Absorbance Infra-red Spectrum having an Aliphatic C-H Area to Aromatic C-H Area ratio of at least 10.

19. The process of claim 18, wherein the crosslinking agent is selected from diepoxycyclooctane, diepoxyoctane, 1,3-butadiene diepoxide, glycerol diglycidyl ether, bisphenol A diglycidyl ether, 1,4-butanediol diglycidyl ether, 1,4-cyclohexanedimethanol diglycidyl ether, bisphenol F diglycidyl ether, neopentyl glycol diglycidyl ether, polypropylene glycol) diglycidyl ether, and mixtures thereof.

20. The process of claim 19, wherein the hydrocarbon feedstream is a naphtha with a boiling range of about 80 to about 450° F. (27 to 232° C.), and contains aromatic and non-aromatic hydrocarbons.

21. A process for separating aromatics from a hydrocarbon feedstream containing aromatics and non-aromatics comprising:
  a) contacting a first polymeric membrane assembly with a first carbon weight aromatic cut-point, resulting in a first retentate and a first permeate; and
  b) contacting the first permeate with a second polymeric membrane assembly with a second carbon weight aromatic cut-point, wherein the second carbon weight aromatic cut-point that is lower than the first carbon weight aromatic cut-point of the first polymeric membrane assembly, resulting in a second retentate and a second permeate,
wherein no more than two consecutive carbon weight aromatics comprise at least 75 wt % of the total aromatics in the second permeate, and wherein the combined wt % of the two consecutive carbon weight aromatics in said second permeate is at least 100% greater than the combined wt % of the two consecutive carbon weight aromatics in the hydrocarbon feedstream, and
wherein the first and second membrane assemblies are each composed of a top layer of polymer film, a bottom layer of polymer film, and from 2 to 6 polymeric membrane elements disposed therebetween, and wherein each polymeric membrane element is comprised of a middle layer of a porous polytetrafluoroethylene film having a pore size from about 0.1 to about 0.3 microns surrounded on top and bottom with cast polymer layers comprised of a dianhydride, a diamine, a cross-linking agent and a difunctional dihydroxy polymer selected from:

a) dihydroxy end-functionalized ethylene propylene copolymers with an ethylene content from about 25 wt % to about 80 wt %;
b) dihydroxy end-functionalized ethylene propylene diene terpolymers with an ethylene content from about 25 wt % to about 80 wt %;
c) dihydroxy end-functionalized polyisoprenes; dihydroxy end-functionalized polybutadienes; dihydroxy end-functionalized polyisobutylenes;
d) dihydroxy end-functionalized acrylate homopolymers, copolymers and terpolymers; dihydroxy end-functionalized methacrylate homopolymers, copolymers and terpolymers; and mixtures thereof, wherein the mixtures of acrylate and methacrylate monomers range from C1 to C18;
e) dihydroxy end-functionalized condensation homopolymers, copolymers, terpolymers and higher order compositions of structurally different monomers, including alcohol-terminated end-functionalized esters and dihydroxy end-functionalized multimonomer polyesters; and mixtures thereof, wherein the polyalkyladipate structures range from $C_1$ to $C_{18}$;
f) dihydroxy end-functionalized perfluoroelastomers;
g) dihydroxy end-functionalized urethane homopolymers, copolymers, terpolymers, and higher order compositions of structurally different monomers;
h) dihydroxy end-functionalized carbonate homopolymers, copolymers, terpolymers, and higher order compositions of structurally different monomers;
j) dihydroxy end-functionalized ethylene alpha-olefin copolymers; dihydroxy end-functionalized propylene alpha-olefin copolymers; and dihydroxy end-functionalized ethylene propylene alpha-olefin terpolymers; wherein the alpha-olefins are linear or branched and range from $C_3$ to $C_{18}$;
j) dihydroxy end-functionalized styrene homopolymers, copolymers, terpolymers, and higher order compositions of structurally different monomers;
k) dihydroxy end-functionalized silicone homopolymers, copolymers, terpolymers, and higher order compositions of structurally different monomers;
l) dihydroxy end-functionalized styrene butadiene copolymers; dihydroxy end-functionalized styrene isoprene copolymers; and
m) dihydroxy end-functionalized styrene butadiene block copolymers; and dihydroxy end-functionalized styrene isoprene block copolymers.

22. The process of claim 21, wherein each at least one polymeric membrane element of the membrane assembly is comprised of a hard segment and a soft segment, wherein the soil segment has a glass transition temperature, $T_g$, of less than 77° F. (25° C.), and wherein the at least one polymeric membrane element exhibits an Absorbance Infra-red Spectrum having an Aliphatic C-H Area to Aromatic C-H Area ratio of at least 10.

23. The process of claim 22, wherein the crosslinking agent is selected from diepoxycyclooctane, diepoxyoctane, 1,3-butadiene diepoxide, glycerol diglycidyl ether, bisphenol A diglycidyl ether, 1,4-butanediol diglycidyl ether, 1,4-cyclohexanedimethanol diglycidyl ether, bisphenol F diglycidyl ether, neopentyl glycol diglycidyl ether, poly(propylene glycol) diglycidyl ether, and mixtures thereof.

24. The process of claim 23, wherein the hydrocarbon feedstream is a naphtha with a boiling range of about 80 to about 450° F. (27 to 232° C.), and contains aromatic and non-aromatic hydrocarbons.

* * * * *